US 9,421,118 B2

(12) United States Patent
Cropper et al.

(10) Patent No.: US 9,421,118 B2
(45) Date of Patent: Aug. 23, 2016

(54) DIGITAL CONTROL STRAP SYSTEM

(75) Inventors: Dean F. Cropper, Ashland, OR (US); Lowell Scott Weil, Sr., Glenview, IL (US); Lowell Scott Weil, Jr., Lake Forest, IL (US)

(73) Assignee: Royal Patents, LLC, Ashland, OR (US)

( * ) Notice: Subject to any disclaimer, the term of this patent is extended or adjusted under 35 U.S.C. 154(b) by 764 days.

(21) Appl. No.: 13/044,523

(22) Filed: Mar. 9, 2011

(65) Prior Publication Data

US 2012/0232453 A1  Sep. 13, 2012

Related U.S. Application Data

(60) Provisional application No. 61/450,618, filed on Mar. 8, 2011.

(51) Int. Cl.
*A61F 5/00* (2006.01)
*A61F 13/00* (2006.01)
*A61F 5/01* (2006.01)
*A61F 5/042* (2006.01)
*A61F 5/37* (2006.01)

(52) U.S. Cl.
CPC .................. *A61F 5/019* (2013.01); *A61F 5/042* (2013.01); *A61F 5/3715* (2013.01)

(58) Field of Classification Search
CPC ...... A61F 13/063; A61F 13/066; A61F 5/019; A61F 5/11; A61F 5/05875; A61F 5/0118; A43B 7/26
USPC ........... 602/30, 63, 65, 22, 66; D24/190–192; 2/22
See application file for complete search history.

(56) References Cited

U.S. PATENT DOCUMENTS

| | | | | |
|---|---|---|---|---|
| 1,746,865 A * | 2/1930 | Page | ............................... | 602/30 |
| 1,785,185 A * | 12/1930 | Day | ............................... | 602/30 |
| 2,596,038 A * | 5/1952 | Mayer | ........................... | 602/30 |
| 3,063,446 A * | 11/1962 | Levitt | ............................. | 602/30 |
| 4,632,103 A * | 12/1986 | Fabricant et al. | ............... | 602/30 |
| 4,644,940 A * | 2/1987 | Nakamura | ...................... | 602/30 |
| 5,282,782 A * | 2/1994 | Kasahara | ....................... | 602/30 |
| 5,735,807 A | 4/1998 | Cropper | | |
| 5,772,621 A * | 6/1998 | Unruh | ............................. | 602/30 |

FOREIGN PATENT DOCUMENTS

GB  225330 A  * 12/1924

* cited by examiner

*Primary Examiner* — Kim Lewis
(74) *Attorney, Agent, or Firm* — Durham Jones & Pinegar, P.C., Intellectual Property Law Group

(57) ABSTRACT

A digital strapping system comprising an alternatively configurable hallux strap system for positioning and exercising a hallux of a foot, and/or an alternatively configurable osteotomy strap system for positioning and exercising a second and/or third digit of a foot.

27 Claims, 22 Drawing Sheets

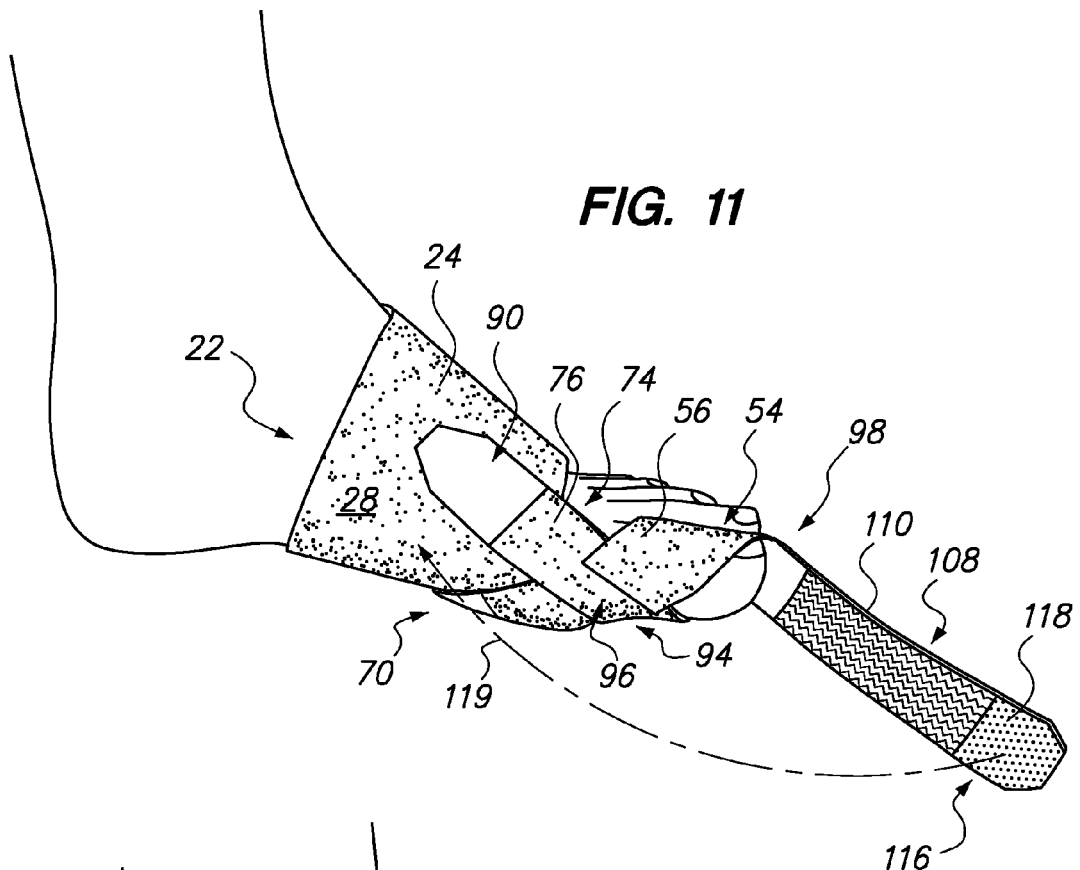

DIGITAL CONTROL STRAP SYSTEM

FIELD OF THE INVENTION

This invention relates generally to a digital or toe strapping system and/or method and, in particular, to a digital or toe strapping system and/or method comprised of a hallux control strap system and/or an osteotomy strap system.

BACKGROUND OF THE INVENTION

Currently, correct digit or toe positioning following surgery, is given little attention and although corrective toe surgery realigns skeletal structure, little is done to address soft tissue correction. For example, distorted joints that arise from a number of mechanical imbalances and genetic issues are corrected using various surgical interventions; however, due to the malaligned skeletal structure, the surrounding connective soft tissue, i.e., muscle, tendons, ligaments, and joint capsule, heal in unnatural positions. Accordingly, the soft tissue is in imbalance in either flaccid or contractured positions even though the skeletal structure has been surgically corrected. Hence, if left alone, the surgical procedure can be compromised allowing scar tissue formation to occur in a non-anatomical position, which can lead to complications, longer rehabilitation time or another surgical procedure. Some of these complications are floating toe, which occurs after a Weil osteotomy with complication reports as high as thirty percent or complications following bunionectomies such as hallux rigidus or re-occurrence of hallux valgus.

One modality for digit range of motion is manually stretching, by the patient or a physical therapist. This method is cumbersome and not particularly effective since it requires patient discipline. Non-compliance by the patient is high, which contributes to a high post-operative complication rate. Moreover, there is no practical way to properly exercise the digits following surgery.

Thus, there is a need for a system that overcomes one or more of the significant shortcomings delineated hereinabove.

BRIEF SUMMARY OF ONLY SEVERAL ASPECTS OF THE INVENTION

Accordingly, and in one aspect, one embodiment of the invention is directed to a digital strapping system comprising a hallux strap system and/or an osteotomy strap system, used alone, or in simultaneous or sequential combination with one or more other like or different digital strapping system(s).

In one aspect, the hallux strap system is a hallux control strap system, comprising a hallux pocket portion, at least a part of which is configured to at least partially receive or abut against a hallux of a foot; a first strap member extending from the hallux pocket portion and terminating to a first free end; a second strap member extending from the hallux pocket portion and terminating to a second free end; the first and second strap members configured to cross after extending from the hallux pocket portion and before terminating to the first and second free ends for defining a substantially parallel or cruciate strap configuration extending from the hallux pocket portion and terminating to the first and second free ends, wherein the first and second strap members are alternately configurable to extend at a variety of angles with respect to one another, but are attached to the hallux pocket portion so as to extend at about a 30 degree to about a 180 degree angle with respect to each other when both are in an unwrapped and unfolded single coplanar state; and means for removably anchoring the first and second free ends to a covered or naked portion of the foot.

In another aspect, the osteotomy strap system comprises a mid-foot circumscribing strap member, sleeve or sock configured to encircle at least a mid-foot location of a foot of a patient; an osteotomy strap comprising:

a toe encircling strap member configured to closely and entirely encircle substantially all of a length of at least one toe;

an elongated base member substantially perpendicular with and attached to the toe encircling strap member; and means for attaching said elongated base member to varying positions along a plantar surface of said mid-foot circumscribing strap member, sleeve, or sock to splint at least the one surgical toe of the patient in a splinted, plantarflexed position.

In one aspect, and in one configuration, yet another aspect of one embodiment of the invention is directed to any device, system, apparatus or method comprising any one or more of the above-recited features and/or any one or more of the specific features recited herein below, used singly or in any combination, whether including past or future known feature(s) or not.

BRIEF DESCRIPTION OF THE DRAWINGS

In the accompanying drawings, which form a part of the specification and are to be read in conjunction therewith, and in which like reference numerals are used to indicate like parts in the various views:

FIG. 11 is a side perspective view of an embodiment of the hallux control strap system of FIG. 9 receiving at least a portion of the hallux of the foot of the patient and illustrating the first and second strap members operatively coupled to the calibrated mid-foot compression strap, and also illustrating the second strap member threaded through the first strap member forming a crossing or intersection of the cruciate strap configuration of the first and second strap members, and further illustrating a wrapping direction of one embodiment of an elastic band member of the hallux control strap for adjustably coupling the elastic band member to the calibrated mid-foot compression strap;

FIG. 12 is a side perspective view of an embodiment of the hallux control strap system of FIG. 9 applied to the foot of the patient and illustrating the elastic band member of the hallux control strap overlying the crossing of the cruciate strap configuration of the first and second strap members and further illustrating the coupling of the elastic band member to the calibrated mid-foot compression strap for applying an additional abduction force or pressure to the hallux when the hallux control strap system of FIG. 9 is in one embodiment of a hallux valgus control and/or varus configuration;

DETAILED DESCRIPTION OF THE INVENTION

In one aspect of the invention, one embodiment is directed to anyone or more of: (1) a hallux control strap system, (2) a method of providing hallux control, (3) an osteotomy strap system, and (4) a method of providing osteotomy therapy. Any single or plurality of embodiments of any and/or some and/or all of these may be provided together or alone, simultaneously and/or in any sequence with each other—and in any combination thereof.

Figure 1:
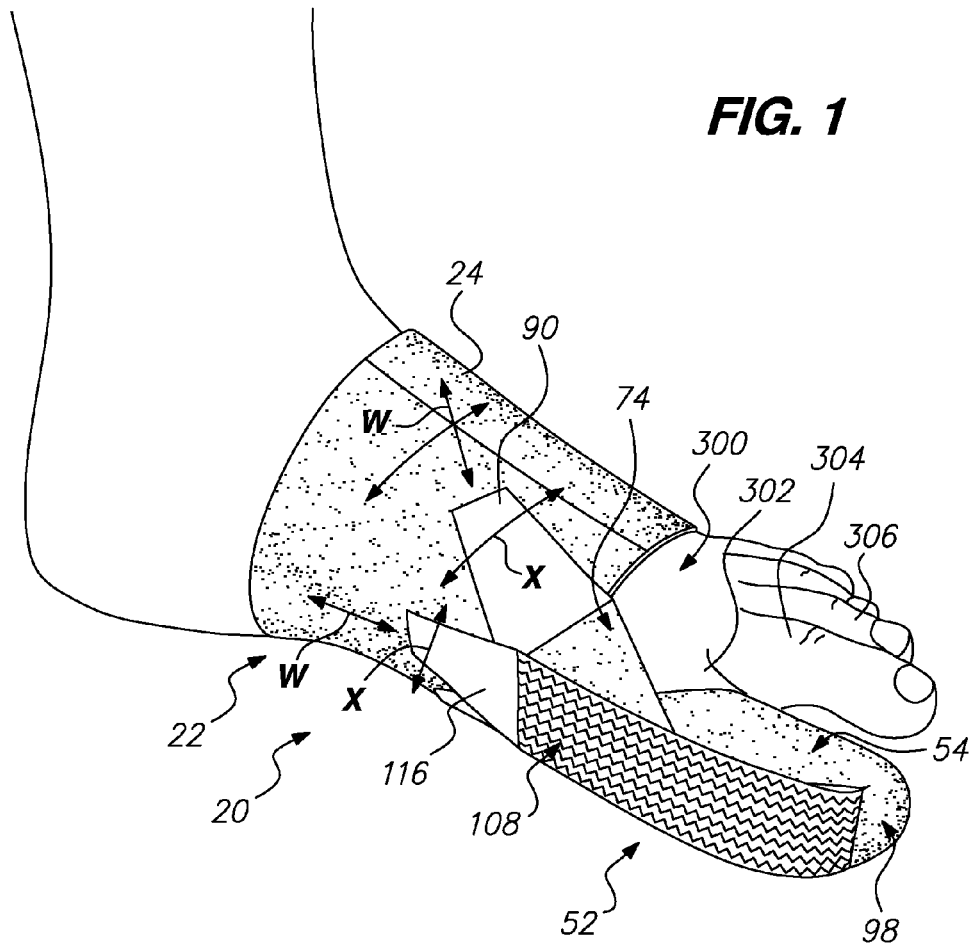
FIG. 1 is a top, side, and front perspective view of an embodiment of a hallux control strap system applied to a foot of a patient, which is alternately configurable along any combination of, e.g., bi-directional arrows W and X.
Figure 2:
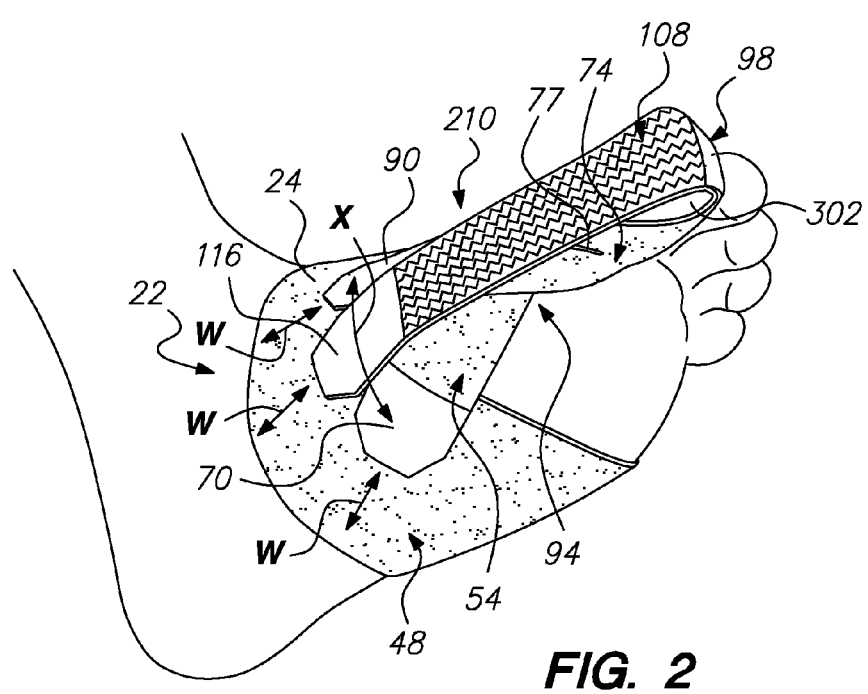
FIG. 2 is a bottom, side, and front perspective view of an embodiment of the hallux control strap system of FIG. 1 applied to the foot of the patient.

FIGS. 1 and 2 illustrate an embodiment of a digital or toe strapping system comprised of hallux control strap system 20. In one embodiment, hallux control strap system 20 comprises only a hallux control strap 52. In another embodiment hallux cnotrol strap system 20 also comprises a calibrated mid-foot compression strap 22. In one embodiment, calibrated mid-foot compression strap 22 is replaced by another covering or other foot securing device such as a sock, sleeve, compression sock, compression sleeve, or elongated strap member that fits around an instep, ankle, or upper ankle. In one embodiment these comprise breathable fabric such as disclosed in U.S. Pat. No. 5,735,807, which is herein incorporated by reference in its entirety.

Figure 20:
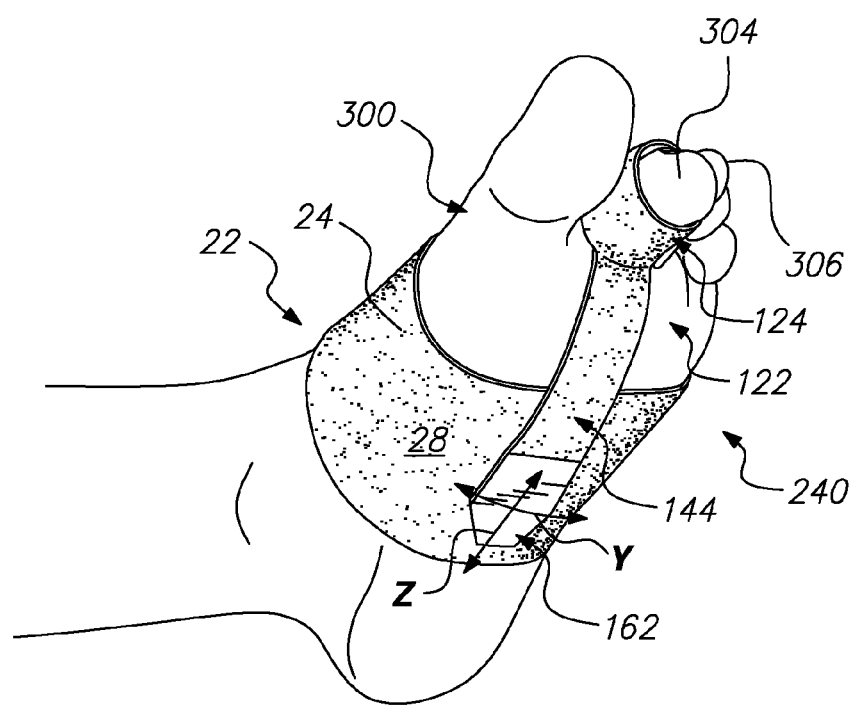
FIG. 20 is a bottom perspective view of an embodiment of the osteotomy strap system of FIG. 19.
Figure 21:
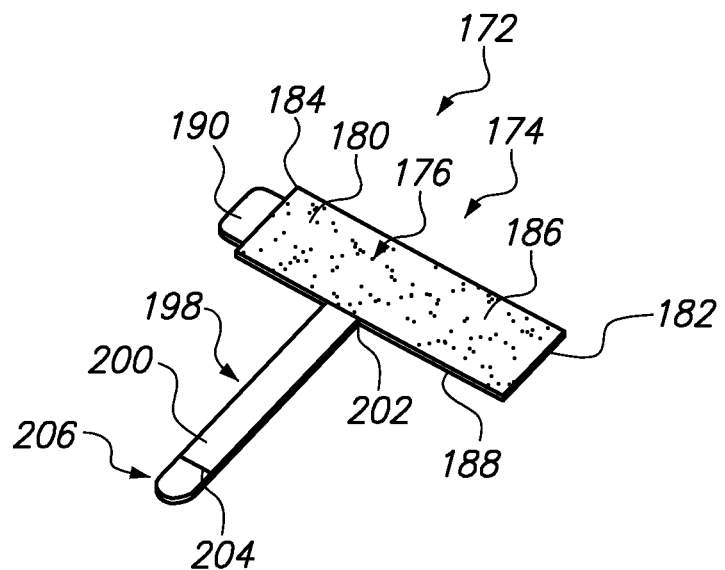
FIG. 21 is an anterior perspective view of an embodiment of an osteotomy exercise strap of one embodiment of an osteotomy strap system.
Figure 22:
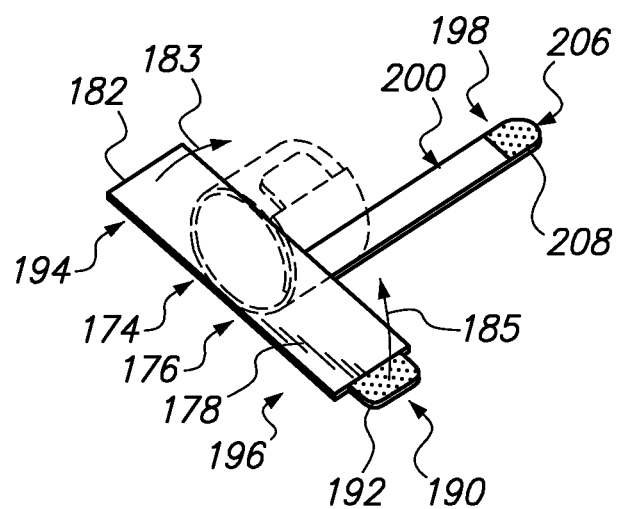
FIG. 22 is a posterior perspective view of the osteotomy exercise strap of FIG. 21 wherein phantom lines indicate one embodiment of a toe-attachment configuration.
Figure 23:
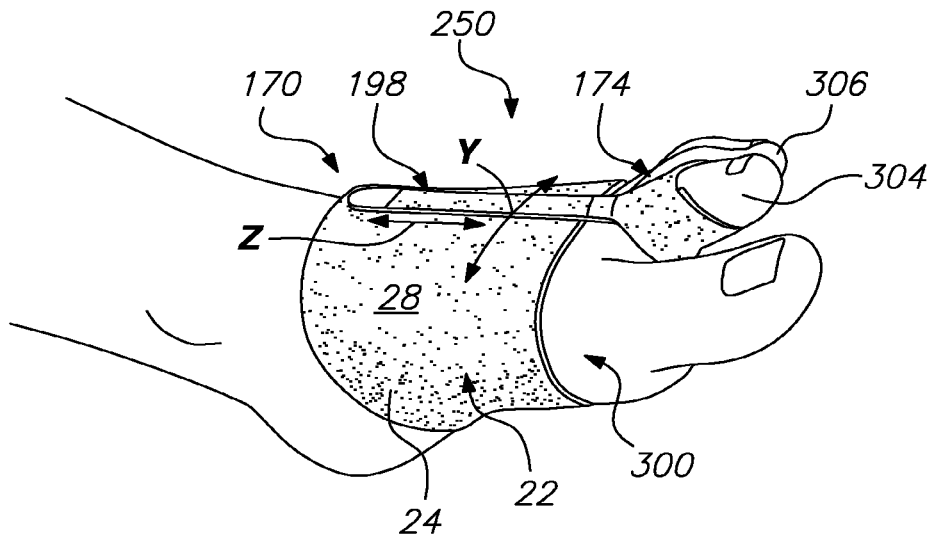
FIG. 23 is a top and side perspective view of an embodiment of an osteotomy strap system comprised of the osteotomy exercise strap of FIG. 21 operatively coupled to a second digit or toe of the foot of the patient and to the calibrated mid-foot compression strap of FIG. 5 in one embodiment of an osteotomy exercise configuration.
Figure 24:
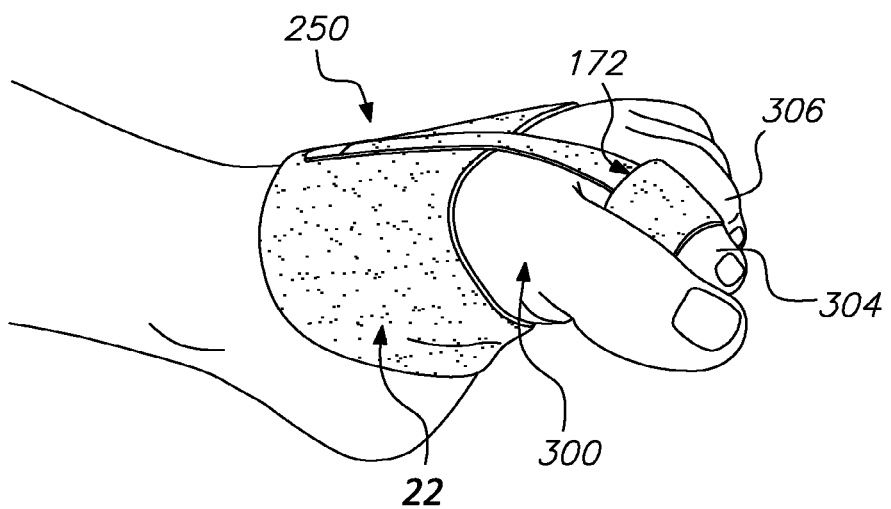
FIG. 24 is a top and side perspective view of an embodiment of an osteotomy strap system comprised of the osteotomy exercise strap of FIG. 21 operatively coupled to the second digit or toe of a foot of a patient and to the calibrated mid-foot compression strap of FIG. 5 in one embodiment of an osteotomy exercise configuration with the second digit or toe flexed from the dorsiflexed position illustrated in FIG. 23 toward a plantar plane of the foot of the patient.

In one embodiment, one or more of the various attachment and stretching or traction strap member(s) and elastic band(s) are variably and independently positionable along any covered or uncovered portion of a foot, thereby making, e.g., hallux control strap 52, variably configurable, such as in accordance with any combination of positions along the extensions of bi-directional arrows W and X. Arrows W generally denote movable positioning substantially along the metatarsal axes, which generally tends to tighten the strap member(s) or band(s). Arrows X generally denote movable positioning transverse to the metatarsal axes, which tightens and transversely redirects the digit. (The above paragraph holds true also for direction arrows Y and Z in FIGS. 20 and 23, described below.).

Referring to FIGS. 1 through 4, and in one embodiment, calibrated mid-foot compression strap 22 (and/or, e.g., any circumscribing member, sock, or sleeve) is comprised of an elongated elasticized body 24 comprised of an inner surface 26, an outer loop surface 28, opposing first and second ends 30 and 32, and opposing first and second longitudinal edges 34 and 36.

In a series of alternate embodiments, any of the straps, configurations, embodiments of configurations, strap systems disclosed herein, or otherwise covered devices, systems or methods within the scope of this invention can be attached to a foot in accordance with any of the various the configurations and/or positionings shown or contemplated herein, by a suitable medical grade skin-safe adhesive, thereby allowing at least one use on a naked foot without any covering.

Inner surface 26 of elongated elasticized body 24 is preferably formed from, but not limited to, a soft hypoallergenic non-slip material that provides a soft but tactile (high coefficient of friction) interface with the skin for minimizing migration of calibrated mid-foot compression strap 22. Additionally, outer loop surface 28 of elongated elasticized body 24 is preferably entirely comprised of a loop type of material defining outer loop surface 28, which is compatible with a hook material for forming a hook and loop type of coupling or attachment. Hook and loop type of materials include, e.g., the commonly known material VELCRO®. In one embodiment, elongated elasticized body 24 is preferably formed from, but not limited to, a material referenced as KT-PS-01 Knew-Tek™ Pigskin Black and sold by HTI Global, Inc., 15 West Finch Street, Broadalbin, N.Y. 12025.

In one embodiment, the use of hook fabric is replaced by the use of loop fabric, and vice-versa. In one embodiment, any combination, and use of any combinations, of hook and loop fabrics on various top and bottom portions of the various straps, foot coverings, and elements described herein, moreover, is also suitable for the various relevant embodiments of this aspect of the invention.

Furthermore, outer loop surface 28 is preferably provided with indicia 38 proximate a first end 30 of elongated elasticized 24. Indicia 38 are comprised of longitudinally spaced-apart vertical level lines and associated numbers indicative of relative compression levels that allow for varying levels of compression to a foot as will be further delineated below.

Still referring to FIGS. 1 through 4, and in one embodiment, calibrated mid-foot compression strap 22 is further comprised of an end portion 40 having an under surface hook portion 42 compatible with outer loop surface 28 of elongated elasticized body 24 for forming a hook and loop type of coupling or attachment between one another. In one embodiment, end portion 40 is separate from elongated elasticized body 24 and, in another embodiment, end portion 40 is fixed to second end 32 of elongated elasticized body 24 by, for example, machine or hand stitching one to the other. If end portion 40 is separate from elongated elasticized body 24, then it is coupled to elongated elasticized body 24 by mounting under surface hook portion 42 of end portion 40 between two portions of outer loop surface 28 of elongated elasticized body 24 wherein one of the two portions is proximate second end 32 of elongated elasticized body 24. If end portion 40is fixed to second end 32 of elongated elasticized body 24, then it is coupled to elongated elasticized body 24 by attaching under surface hook portion 42 of end portion 40 to outer loop surface 28 of elongated elasticized body 24.

Calibrated mid-foot compression strap 22 is provided in a plurality of sizes to accommodate different foot sizes and has a low profile, which is well-suited for use inside normal footwear. Elongated elasticized body 24 of calibrated mid-foot compression strap 22 can be tailored to fit a particular foot size by cutting elongated elasticized body 24 proximate to first end 30 and/or proximate to end portion 40 to a length, and/or also at an angle suitable for various feet. When end portion 40 is separate from elongated elasticized body 24, then elongated elasticized body 24 can be tailored to fit a particular foot size by cutting elongated elasticized body 24 proximate first end 30 and/or second end 32 to an appropriate length, and also to an appropriate angle.

Figure 4:
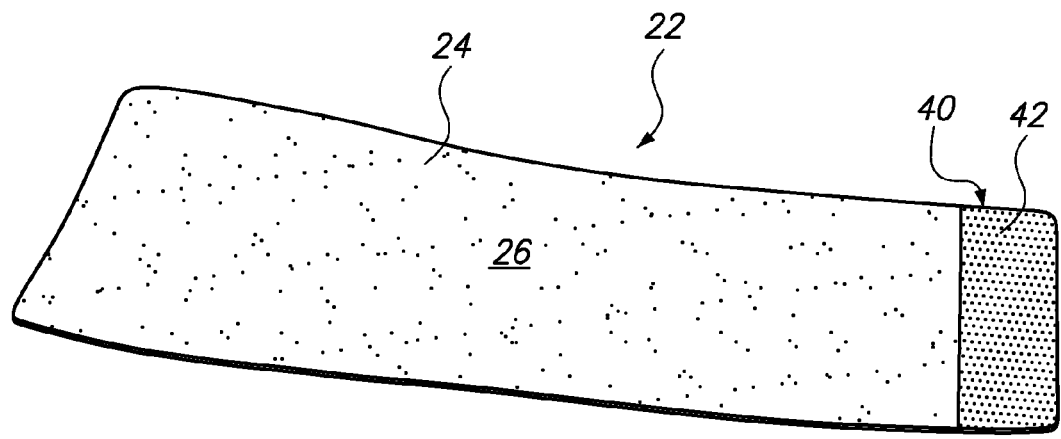
FIG. 4 is a bottom perspective view of the unwrapped calibrated mid-foot compression strap in FIG. 3 of the hallux control strap system.
Figure 5:
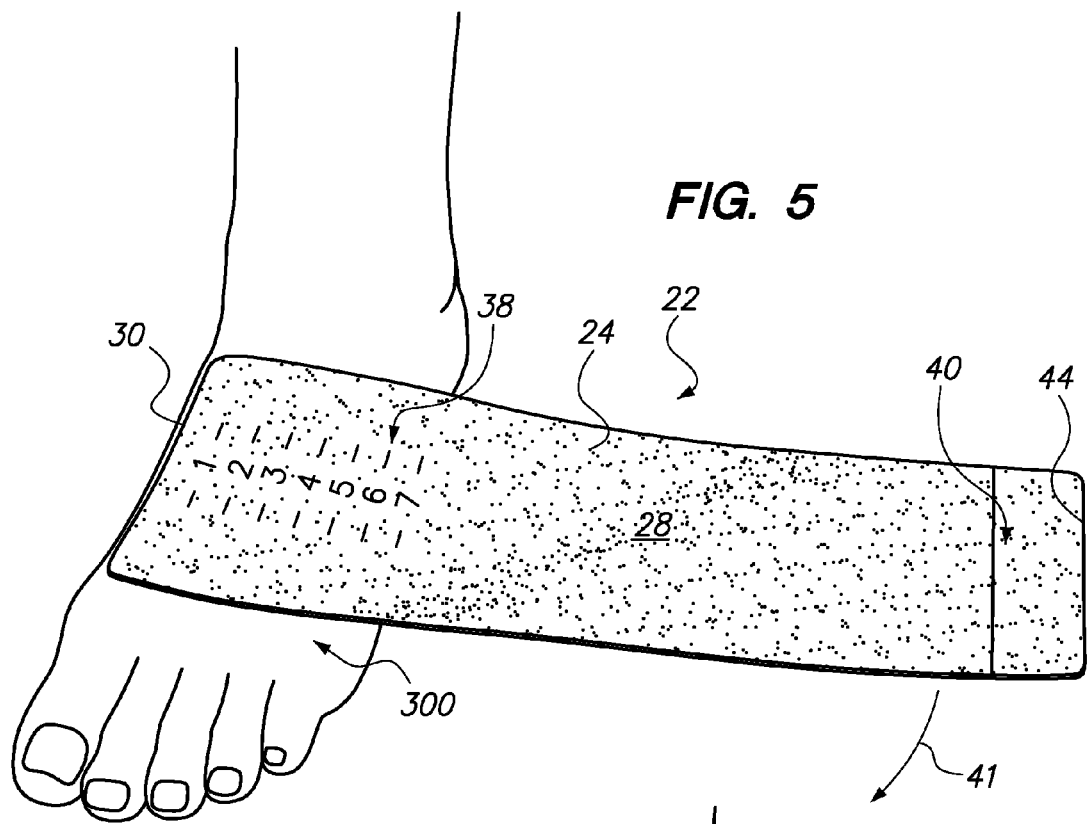
FIG. 5 is a top perspective view of the unwrapped calibrated mid-foot compression strap in FIG. 3 of a hallux control strap system initially positioned on a mid-foot of the patient.
Figure 6:
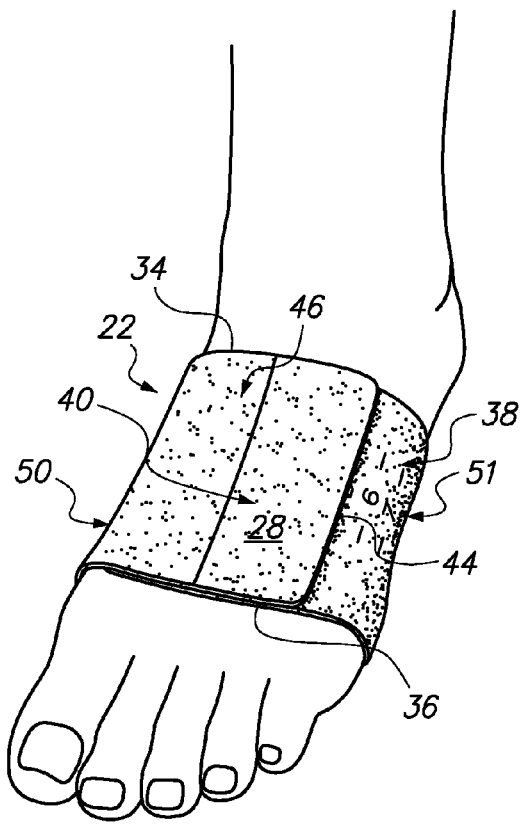
FIG. 6 is a top perspective view of the calibrated mid-foot compression strap in FIG. 3 of a hallux control strap system in a wrapped, circumscribing configuration about a mid-foot of the patient.

Referring to FIGS. 5 and 6, and in general, calibrated mid-foot compression strap 22 is wrapped around a foot 300 of a patient preferably at a mid-foot location by placing first end 30 of elongated elasticized body 24 on a dorsal surface of the mid-foot with indicia 38 face-up and wrapping elongated elasticized body 24 around one side of the foot, under the foot, around the other side of the foot, and then coupling or attaching under surface hook portion 42 (FIG. 4) of end portion 40 to outer loop surface 28 of elongated elasticized body 24 at a location that provides a proper level of compression. In order to correctly obtain a proper level of compression, second end 32 or an end 44 of the end portion 40 is located at, or proximal to, one of the level lines and numbers of indicia 38, which is preferably determined by a health care professional. Hence, indicia 38 allow for varying levels of compression to the foot for edema control wherein the setting is preferably controlled by a health care professional.

Accordingly, a method for fitting calibrated mid-foot compression strap 22 to a particular foot may include the steps of determining an amount of compression to put on the particular foot; if necessary, cutting elongated elasticized body 24 so that second end 32 or end 44 is approximately at one of indicia 38 associated with a determined amount of compression; wrapping the mid-foot with elongated elasticized body 24 as delineated above, and attaching second end 32 to elongated elasticized body 24 utilizing end portion 40, as also delineated above.

FIG. 6 illustrates calibrated mid-foot compression strap 22 in position so as to define a calibrated mid-foot compression circumscribing member (or sleeve) configuration having a dorsal outer surface 46, a plantar outer surface 48 (FIG. 2), a medial outer surface 50, and a lateral outer surface 51, which are each correlative to the respective dorsal, plantar, medial, and lateral sides of calibrated mid-foot compression strap 22 panel covers. Additionally, and in use, it is preferred that a portion of second longitudinal edge 36 of calibrated mid-foot compression trap 22 that is adjacent lateral outer surface 51, be positioned at about the base of the fifth metatarsal head for comfort, and that a portion of second longitudinal edge 36 of calibrated mid-foot compression strap 22 that is adjacent to medial outer surface 50 be positioned at about the base of where a bunionectomy is going to be or was performed.

Referring back to FIGS. 1 and 2, and in one embodiment, hallux control strap 52 comprises a first elongated strap member 54 and a second elongated strap member 74 configured to cross one another for forming a cruciate strap configuration 94, a hallux pocket or concave portion 98, and a third strap or elastic band member 108.

In one embodiment, at least a portion of hallux pocket or concave portion 98 encloses at least a portion of a hallux. As used herein, however, hallux pocket or concave portion 98 can comprise or consist of any abutment or support piece suitable for restraining, capturing, bearing against, moving, providing traction to, or otherwise physically influencing a hallux by exerting physical pressure against it. Non-limiting suitable materials include, e.g., transparent, translucent, woven, molded, extruded, cured, natural or synthetic material(s), including the non-limiting example formats of netting, webbing, cloth, plastic, leather, wood and/or metal—and any combination thereof.

Referring now to FIGS. 7A through 8B, and in one embodiment, hallux control strap 52 is generally Y-shaped when in an unwrapped, unfolded and uncrossed configuration. In this configuration, hallux pocket or concave portion 98 is generally centrally located between first elongated strap member 54, second elongated strap member 74, and third strap or elastic band member 108. Nevertheless, in various alternate embodiments, hallux pocket or concave portion 98 may be in any shape, out of any object(s), and/or of any material(s) suitable for pressing or abutting against a hallux, including any additional shapes/objects/materials that extend away from a point, or varying multiple points, of hallux contact, and/or away from a central location along first elongated strap member 54, second elongated strap member 74 and third strap or elastic band member 108.

The first and second elongated strap members 54 and 74 are attached to and divergently extend away from hallux pocket or concave portion 98 thereby forming about a 70-90 degree angle between the first and second elongated strap members 54 and 74 that defines a crotch area 106. (This angle may however be between about 10° and about 180°, for example, between about any of the following illustrative ranges: 10-170, 20-180, 40-180, 50-180, 60-180, 70-180, 80-180, 90-180, 100-180, 110-180, 120-180, 130-180, 40-60, 40-70, 40-80, 40-90, 40-100, 40-110, 40-120, 40-130, 40-140, 40-150, 40-160, 40-170, 40-180, 70-80, 70-90, 70-100, 70-110, 70-120, 70-130, 70-140, 70-150, etc. . . . ). When laid flat, each of first and second elongated strap members 54 and 74, and third strap or elastic band member 108 extends straight, and radially, as if spokes extending from a hub.

In one embodiment, the angle between two non-stretch first and second elongated strap members 54 and 74 is 90 degrees, +/− about 10 degrees. The convergence of these two straps is cut at a concave angle so hallux control strap 52 will contour to the roundness at the end of a hallux to give a more comfortable and more precise fit. The cut is about a 1.375 inch long curved cut at the end of each strap member, which forms an arc that defines a circle with about a 2.25 inch radius. In one embodiment, ends of only two strap members and a single 1 inch wide elastic band member (such as from Narrow Fabric Indus. Corp. of West Reading, Pa.) are sewn together to create a cup-like shape at their trilateral convergence. However, alternate various other cuts, widths, cut shapes and lengths suitable for applying force against a hallux can be used, as determined, for example, by the use of more than three straps and/or elastic bands, and/or various and independently determined widths of strap members and/or band members. Several non-limiting such embodiments include two elastic bands and two strap members all having the same widths, two-four elastic bands and one strap member all having differing widths, and two elastic bands and one strap member, for example.

At a location distal from hallux pocket or concave portion 98, first and second elongated strap members 54 and 74 respectively terminate at a first free end portion 70 having a first tapered end and a second free end portion 90 having a second tapered end. Third strap or elastic band member 108 is attached to and extends from hallux pocket or concave portion 98 at a location opposing crotch area 106 or the angle formed by the parting of first and second elongated strap members 54 and 74 and terminates to a third free end portion 116 having a third tapered end. The extension of third strap or elastic band member 108 between first and second elongated strap members 54 and 74 forms two additional angles. In one embodiment these two angles between third strap or elastic band member 108 and respective first and second elongated strap members 54 and 74 are the same or nearly the same, but can vary considerably.

In one embodiment, first elongated strap member 54 is comprised of a first elongated elasticized body 56 having opposing longitudinal edges 58 and 60, a first inner surface 62, a first outer loop surface 64, a first end 66, and a second end 68 attached to first free end portion 70 by, for example, machine or hand stitching.

First free end portion 70 includes an under surface hook portion 72 compatible with outer loop surface 28 of elongated elasticized body 24 of calibrated mid-foot compression strap 22 for forming a hook and loop type of coupling or attachment between the two. First inner surface 62 is formed from, but not limited to, a soft hypoallergenic non-slip material that provides a soft but tactile (high coefficient of friction) interface with the skin for minimizing migration of hallux control strap 52. Additionally, first outer loop surface 64 is entirely comprised of a loop type of material for defining first outer loop surface 64.

In one embodiment, first elongated elasticized body 56 is formed from, but not limited to, a material referenced as KT-PS-01 Knew-Tek™ Pigskin Black and sold by HTI Global, Inc., 15 West Finch Street, Broadalbin, N.Y. 12025, wherein this material provides soft hypoallergenic non-slip first inner surface 62 and first outer loop surface 64 of first elongated elasticized body 56.

Similar to first elongated strap member 54, second elongated strap member 74 is comprised of a second elongated elasticized body 76 having opposing longitudinal edges 78 and 80, a second inner surface 82, a second outer loop surface 84, a first end 86, and a second end 88 attached to second free end portion 90 by, for example, machine or hand stitching.

Second free end portion 90 includes an under surface hook portion 92 compatible with outer loop surface 28 of elongated elasticized body 24 of calibrated mid-foot compression strap 22 for forming a hook and loop type of coupling or attachment between the two.

Second inner surface 82 is preferably formed from, but not limited to, a soft hypoallergenic non-slip material that provides a soft but tactile (high coefficient of friction) interface with the skin for minimizing migration of hallux control strap 52. Additionally, second outer loop surface 84 is preferably entirely comprised of a loop type of material for defining a second outer loop surface 84.

In one embodiment, second elongated elasticized body 76 is formed from, but not limited to, a material referenced as KT-PS-01 Knew-Tek™ Pigskin Black and sold by HTI Global, Inc., 15 West Finch Street, Broadalbin, N.Y. 12025, wherein this material provides soft hypoallergenic non-slip second inner surface 82 and second outer loop surface 84 of second elongated elasticized body 76.

Figure 7A:
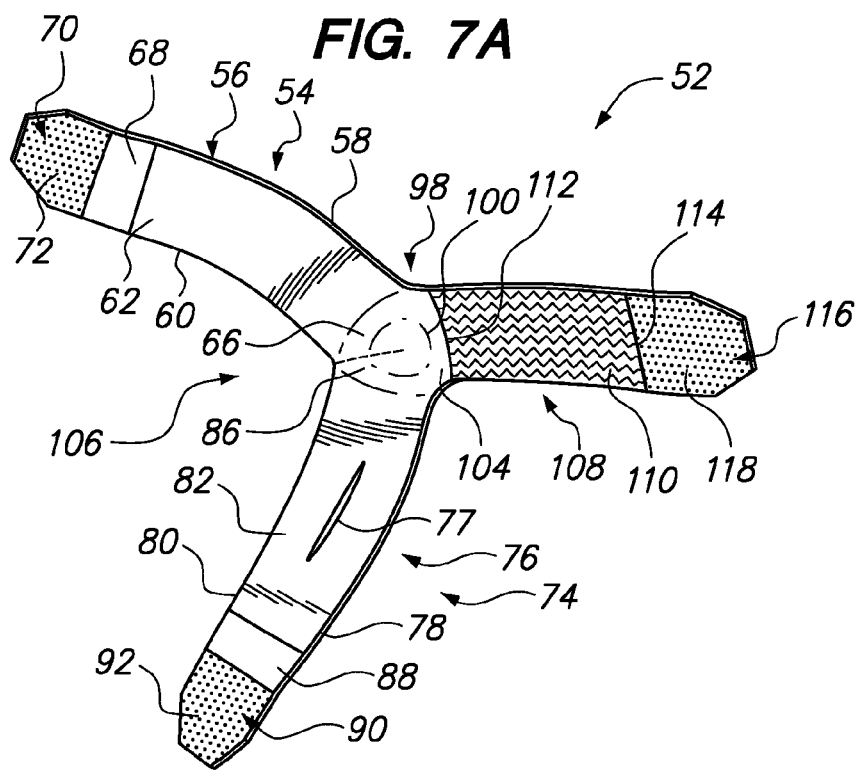
FIG. 7A is a posterior perspective view of an embodiment of a hallux control strap of the hallux control strap system illustrated in FIG. 1.
Figure 7B:
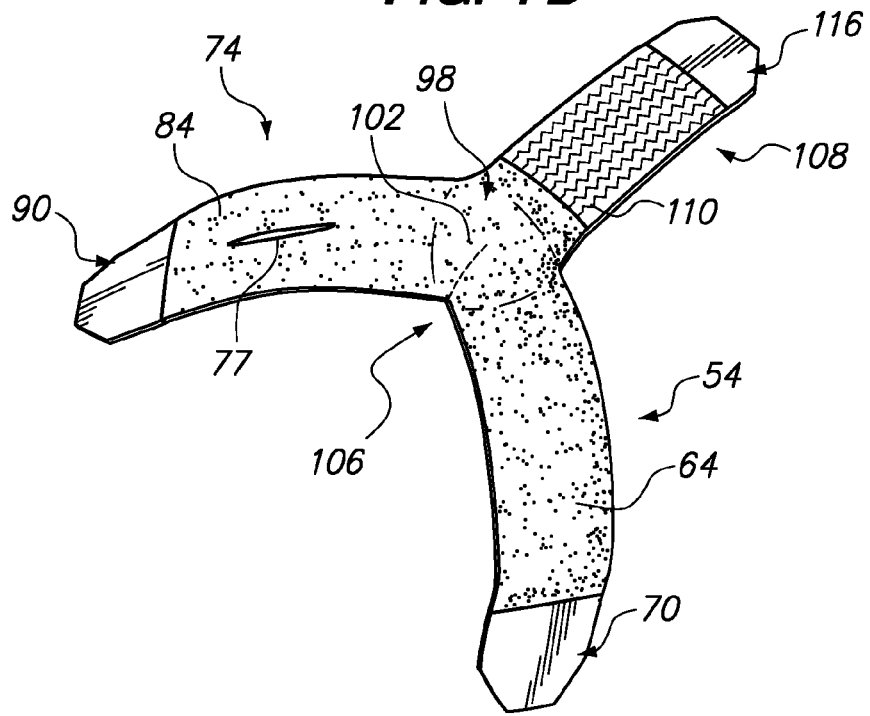
FIG. 7B is an anterior perspective view of the hallux control strap in FIG. 7A of a hallux control strap system.
Figure 10:
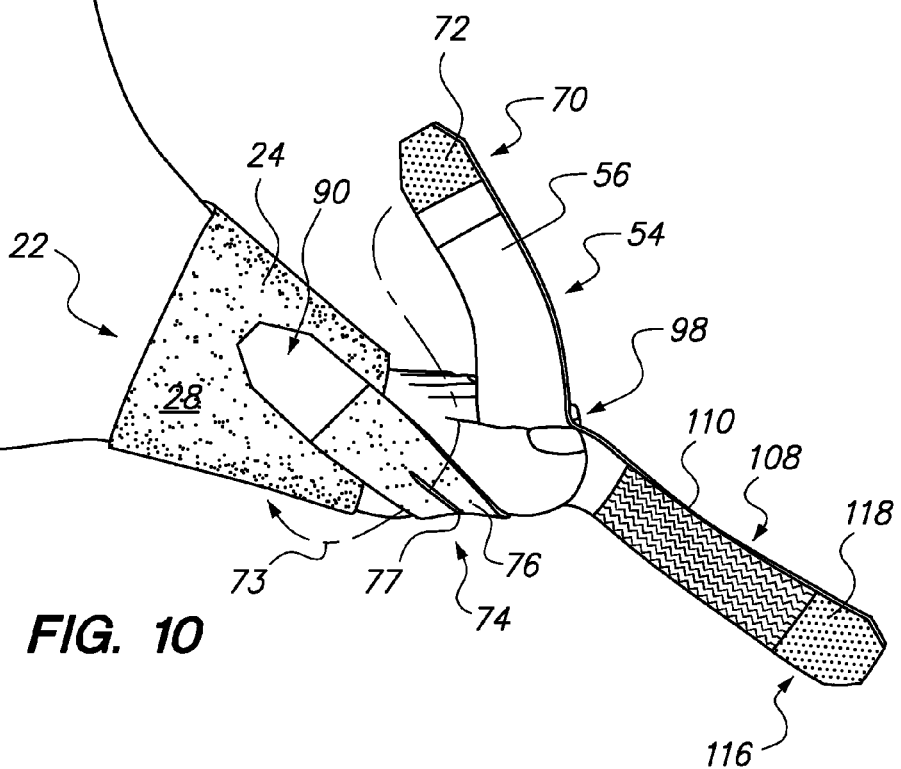
FIG. 10 is a side perspective view of the hallux control strap of FIG. 9 receiving at least a portion of the hallux of the foot of the patient and illustrating the second strap member operatively coupled to the calibrated mid-foot compression strap and further illustrating a wrapping, threading, and coupling direction of an embodiment of a first strap member of the hallux control strap for wrapping the first strap member around the hallux, threading the first strap member through a slit in the second strap member, and coupling the first strap member to the calibrated mid-foot compression strap for forming a cruciate strap configuration that forms a hallux valgus control and/or varus configuration.

Referring to FIGS. 7A and 7B, and in one embodiment, second elongated strap member 74 further comprises a slit 77 (and/or a slot, hole or other aperture(s)) disposed through second elongated elasticized body 76 through which first elongated strap member 54 threads through by taking, for example, a path 73 illustrated in FIG. 10 for forming a cruciate strap configuration 94 having a crossing 96 of first and second elongated strap members 54 and 74, as illustrated in at least FIG. 11. In this cruciate strap configuration 94, a first portion or area of first elongated strap member 54 overlaps second elongated strap member 74 prior to entering slit 77 and a second portion or area of first elongated strap member 54 passes under second elongated strap member 74 after passing through slit 77. Alternatively, the first portion or area of first elongated strap member 54 passes under second elongated strap member 74 prior to entering slit 77 and the second portion or area of first elongated strap member 54 overlaps second elongated strap member 74 after passing through slit 77.

In one configuration, slit 77 is disposed in second elongated strap member 74 at a location that aligns the crossing of first and second elongated strap members 54 and 74 at a general location of the first metatarsal phalangeal joint of the foot or, more specifically, the crossing of first and second elongated strap members 54 and 74 abuts against the medial exterior surface of the foot proximate the first metatarsophalangeal joint.

In another embodiment, first elongated strap member 54 has a slit 77, but second elongated strap member 74 does not or both have at least one or a series of such apertures, so that one may thread over and through the other accordingly.

Figure 8A:
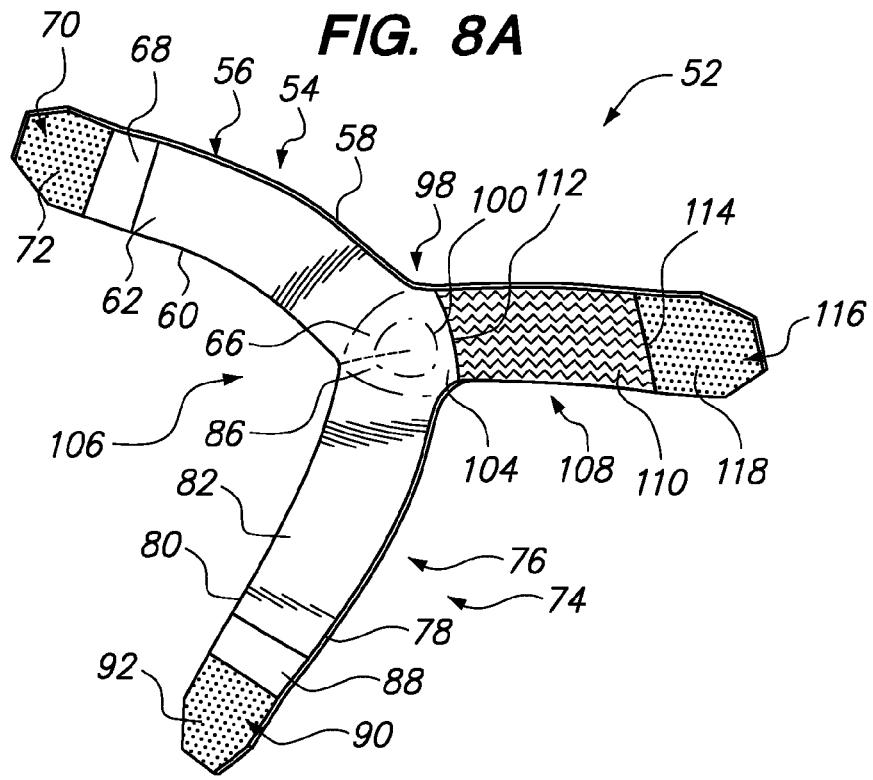
FIG. 8A is a posterior perspective view of an embodiment of a hallux control strap of a hallux control strap system without a slit, slot, hole or other aperture.
Figure 8B:
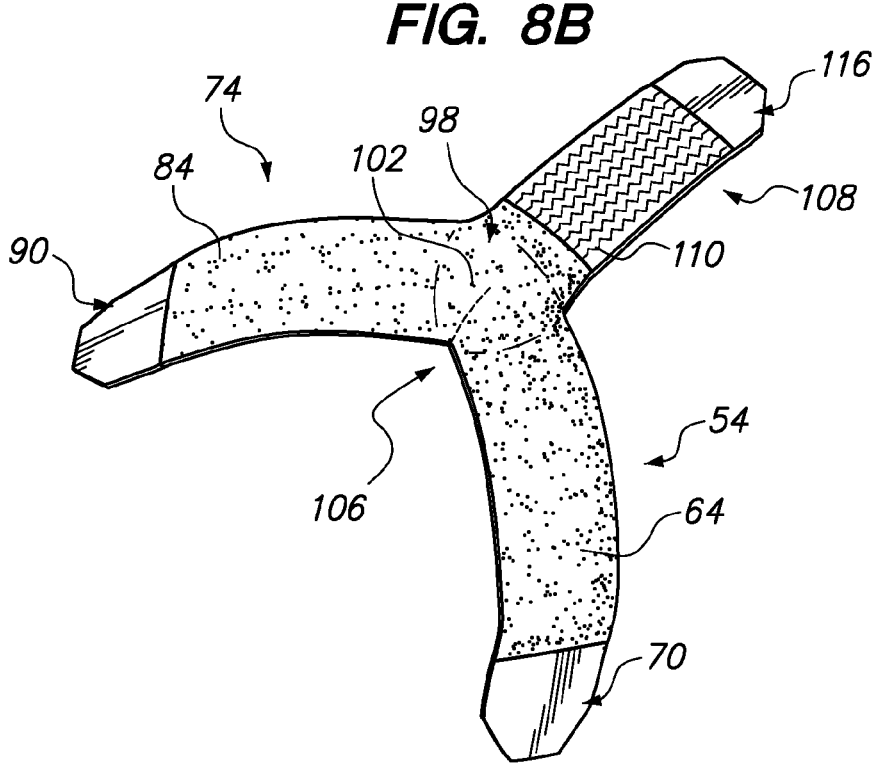
FIG. 8B is an anterior perspective view of the hallux control strap in FIG. 8A.

Referring to FIGS. 8A and 8B, and in another embodiment, second elongated strap member 74 does not have a slit 77 (or any aperture) and first elongated strap member 54 passes over or under second elongated strap member 74, forming a cruciate strap configuration 94 having a crossing 96 of first and second elongated strap members 54 and 74.

Referring to FIGS. 7A through 8B, hallux pocket or concave portion 98 comprises a concave inner surface 100 and a convex outer surface 102 and is formed by an attachment of first end 66 of first elongated strap member 54 with first end 86 of second elongated strap member 74. This attachment is provided by, for example, machine or hand stitching. Alternatively, first and second elongated strap members 54 and 74 may be attached by being integrally formed with one another at their first ends 66 and 86 for forming hallux pocket or concave portion 98. First ends 66 and 86 juxtapose to form a common end 104 of hallux pocket or concave portion 98 at a location opposing crotch area 106 defined by the angle formed by the parting of first and second elongated strap members 54 and 74.

Third strap or elastic band member 108 is comprised of at least one elasticized body 110 extending between first end 112 and second end 114. In one embodiment, the at least one elasticized body 110 is formed from, but not limited to, a blend of nylon and an elastomer such as that sold under the LYCRA®.

First end 112 of at least one elasticized body 110 is attached to common end 104 of hallux pocket or concave portion 98 at a location opposing crotch area 106 or the angle formed by the parting of first and second elongated strap members 54 and 74. This attachment is provided by, but not limited to, machine or hand stitching.

Second end 114 of at least one elasticized body 110 is attached to third free end portion 116 by, but not limited to, machine or hand stitching. Third free end portion 116 includes an under surface hook portion 118 compatible with outer loop surface 28 of elongated elasticized body 24 of calibrated mid-foot compression strap 22 for providing a hook and loop type of coupling or attachment between the two.

In use and operation, and referring to FIGS. 1, 2, and 9 through 16, hallux control strap system 20 comprises alternatively usable configurations comprised of a hallux valgus control or varus configuration 210, a hallux exercise configuration 220, and a hallux plantar plane splinting configuration 230.

Hallux Valgus Control or Varus Configurations

Bunion surgery corrects a hallux that is in a valgus position, but unless the soft tissue is corrected, it will eventually pull the hallux back into valgus recreating the problem that was just fixed surgically. Accordingly, one challenge is to make sure that the soft tissue realigns itself properly because the toe has had either months or years where the soft tissue had been held in a preoperative position. After surgical correction, therefore, if the hallux is not properly splinted in position, the toe will eventually migrate back into the preoperative valgus position.

Referring to FIGS. 1, 2, 12 and 13, and in several configurations, hallux control strap system 20 provides at least one hallux valgus control or varus configuration 210.

Figure 9:
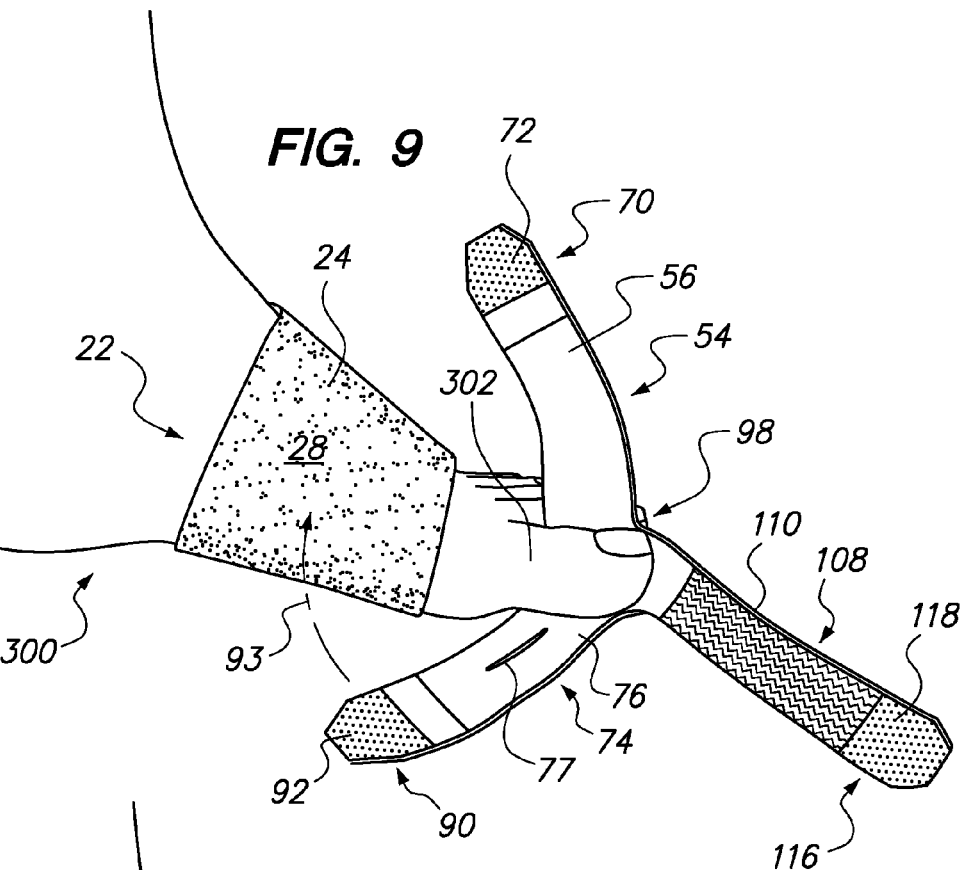
FIG. 9 is a posterior side perspective view of an embodiment of the hallux control strap of FIG. 7A in a position for receiving at least a portion of a hallux of a foot of a patient and illustrating a wrapping direction of an embodiment of a second strap member of the hallux control strap for coupling the second strap member to the calibrated mid-foot compression strap of FIG. 5.

In this configuration, and referring to FIGS. 9 and 10, in one embodiment calibrated mid-foot compression strap 22 of hallux control strap system 20 is applied to a foot 300 of a patient, as delineated above. Next, hallux control strap 52 is operatively applied to foot 300 of the patient by placing concave inner surface 100 (FIG. 7A) of hallux pocket or concave portion 98 on or against the front and lateral side of the hallux 302 of the foot 300 before or after first elongated strap member 54 is threaded or passed through slit 77 of second elongated strap member 74 (or first elongated strap member 54 is passed over or under second elongated strap member 74) for forming cruciate strap configuration 94 (FIG. 11). In this configuration, crossing 96 of first and second elongated strap members 54 and 74 is positioned along the medial side of foot 300 with first and second elongated strap members 54 and 74 divergently extending therefrom in a V-shaped pattern and then terminating to first and second free end portions 70 and 90 utilized by the user to tension cruciate strap configuration 94, and then to secure respective first and second free end portions 70 and 90 via respective paths 73 and 93 to calibrated mid-foot compression strap 22 by coupling or attaching respective under surface hook portions 72 and 92 of respective first and second elongated strap members 54 and 74 to outer loop surface 28 of elongated elasticized body 24 of calibrated mid-foot compression strap 22. With this coupling or attachment, component forces of first and second elongated strap members 54 and 74 sum together and extend down the medial side of the foot 300. More specifically, a summation of force components of first and second elongated strap members 54 and 74 respectively extend in opposite directions or toward the dorsal and plantar sides of the foot 300, thereby stabilizing dorsal and plantar translation and if equal, these opposing forces cancel one another out while a summation of force components of first and second elongated strap members 54 and 74 that extend substantially along the medial side of the foot 300 add together for abducting or separating the hallux 302 from a second toe 304 of the foot 300, thereby opposing valgus forces acting on the hallux 302. When the force components that extend toward the dorsal and plantar surfaces of the foot 300 substantially cancel one another out, the hallux 302 is abducted or separated from the second toe 304 of the foot 300 in a plane that is generally parallel to the plantar plane of the foot 300.

Next, and referring to FIG. 11, third strap or elastic band member 108 is tensioned and passed via a path 119 over a medial side of the hallux 302 and crossing 96 of cruciate strap configuration 94 of first and second elongated strap members 54 and 74 and then attached medially to calibrated mid-foot compression strap 22 to apply an additional abduction force or pressure to hallux 302. This attachment or coupling is provided by under surface hook portion 118 of third free end portion 116 of third strap or elastic band member 108 attaching or coupling to outer loop surface 28 of elongated elasticized body 24 of calibrated mid-foot compression strap 22, thereby providing a hook and loop type of attachment or coupling between the two.

Figure 13:
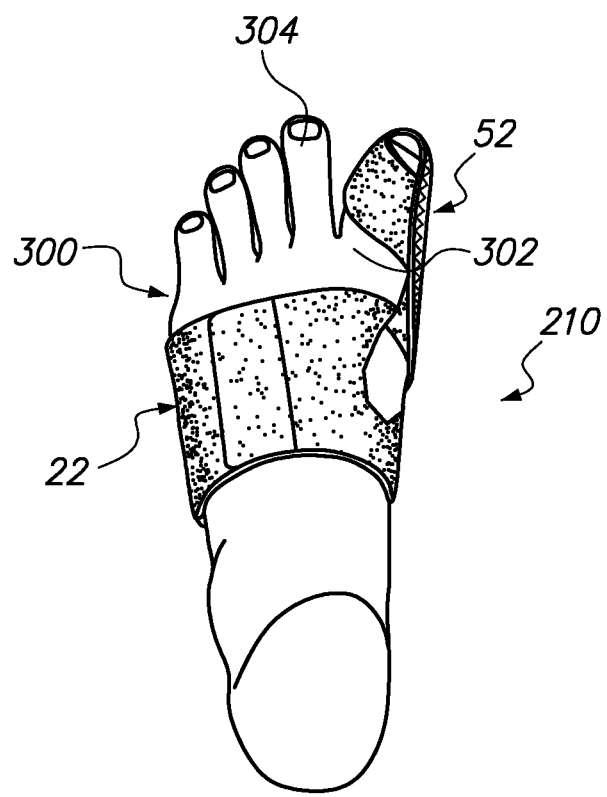
FIG. 13 is a top perspective view of an embodiment of the hallux control strap system of FIG. 9 applied to the foot of the patient in one embodiment of a hallux valgus control and/or varus configuration.

Referring to FIGS. 12 and 13, in one embodiment, hallux control strap 52 is worn by a patient in this hallux valgus control or varus configuration 210 to abduct the great toe or the hallux 302 and put the hallux 302 in a varus position to stabilize and retain the hallux 302 in this position for 6 to 8 weeks post-surgery. After about eight weeks, all the soft tissue generally heals and there is nothing more that can be done with the capsular soft tissue. The Hallux control strap 52 is typically worn in this hallux valgus control or varus configuration 210 at night, throughout the day, and in a walking boot or non-weight bearing apparatus typically worn for the first couple of weeks because of the pain and swelling associated with surgery. There are several different types of surgery for correcting the hallux 302 when the toe is in a valgus position, but all of these types of surgery deal with the same soft tissue healing process. Accordingly, hallux control strap 52 is generally applicable for all the different types of surgery or the correction of the hallux when the toe is in a valgus position.

Exercise Configurations

Figure 14:
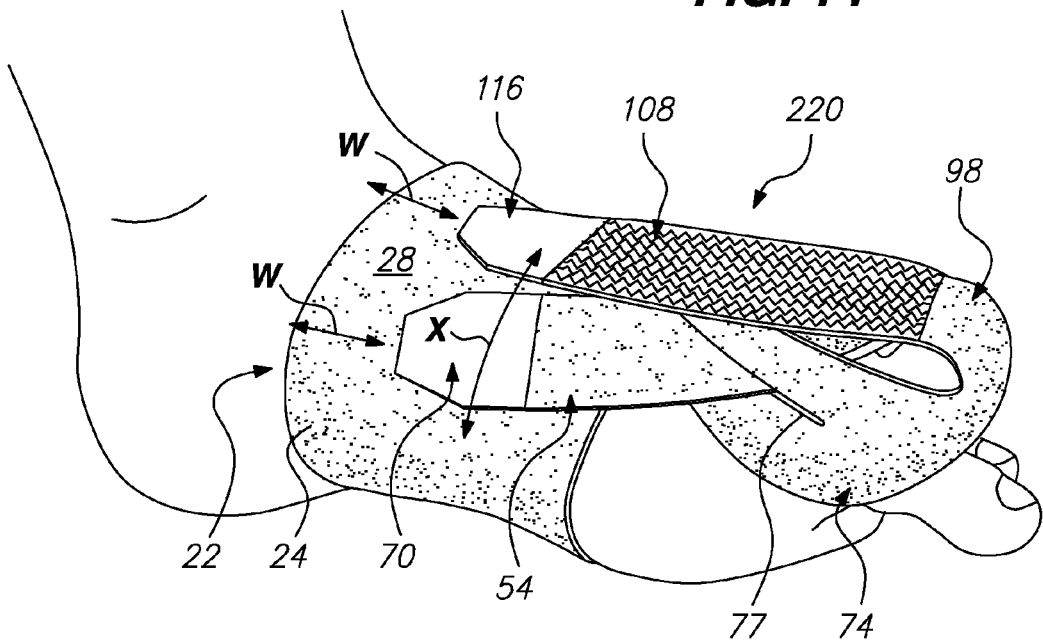
FIG. 14 is a side perspective view of an embodiment of a hallux control strap system applied to a foot of a patient in a hallux exercise configuration with the hallux in a dorsiflexed position.
Figure 15:
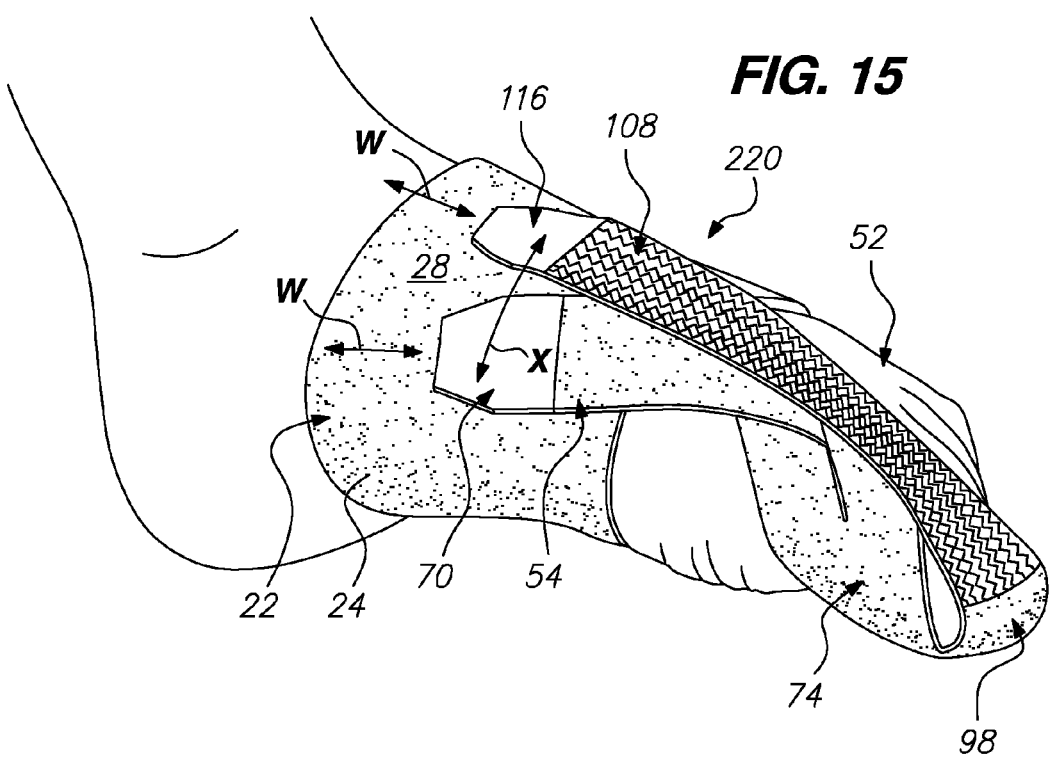
FIG. 15 is a side perspective view of an embodiment of a hallux control strap system applied to a foot of a patient in a hallux exercise configuration and illustrating the hallux flexed from the dorsiflexed position illustrated in FIG. 14 toward a plantar plane of the foot.

Referring to FIGS. 14 and 15, and back to FIGS. 5 through 8, and in several other configurations (determined specifically by and optionally subject to varying adjustment(s) and readjustment(s) per bidirectional arrows W and X), hallux control strap system 20 provides hallux exercise configuration 220, which should only be maintained during an exercise session. In this configuration, (and other similar ones) calibrated mid-foot compression strap 22 of hallux control strap system 20 is applied to the foot 300 of a patient as delineated above. Next, hallux control strap 52 is operatively applied to the foot 300 of the patient by placing concave inner surface 100 of hallux pocket or concave portion 98 on or against the bottom or plantar surface of the hallux 302 before or after first elongated strap member 54 is threaded or passed through slit 77 of second elongated strap member 74 (or, e.g., first elongated strap member 54 is passed over or under second elongated strap member 74) for forming cruciate strap configuration 94. In this configuration, the intersection of first and second elongated strap members 54 and 74 is positioned along the top or dorsal surface of the hallux 302 with first elongated strap member 54 extending from the hallux pocket or concave portion 98 along the lateral side of the hallux 302 and then through the intersection on the dorsal surface of the hallux 302, and with second elongated strap member 74 extending from hallux pocket or concave portion 98 along the medial side of the hallux 302 and then to or through the intersection on the dorsal surface of the hallux 302. First and second elongated strap members 54 and 74 divergently extend from the intersection of cruciate strap configuration 94 in a V-shaped pattern and then terminate to first and second free end portions 70 and 90 utilized by the user to tension cruciate strap configuration 94, and then to secure the respective first and second elongated strap members 54 and 74 to calibrated mid-foot compression strap 22 by coupling or attaching the respective under surface hook portions 72 and 92 of first and second elongated strap members 54 and 74 to outer loop surface 28 of elongated elasticized body 24 of calibrated mid-foot compression strap 22. In one embodiment, first free end portion 70 of first elongated strap member 54 is generally attached or coupled to dorsal outer surface 46 and, perhaps, a little on the medial outer surface 50 of calibrated mid-foot compression strap 22 and second free end portion 90 of second elongated strap member 74 is generally attached or coupled to dorsal outer surface 46 of calibrated mid-foot compression strap 22. With this coupling or attachment, component forces of first and second elongated strap members 54 and 74 sum together and generally extend down the dorsal side of the foot 300 with component forces in the valgus and varus direction generally canceling one another. Next, third strap or elastic band member 108 is tensioned and passed over the top or dorsal side of the hallux 302 and over the intersection of cruciate strap configuration 94 and then, under tension, attached dorsally to calibrated mid-foot compression strap 22 to apply a force or pressure to the hallux 302 which places the hallux 302 in a dorsiflexed position. This attachment or coupling is provided by under surface hook portion 118 of third free end portion 116 of third strap or elastic band member 108 dorsally attaching or coupling to outer loop surface 28 of elongated elasticized body 24 of calibrated mid-foot compression strap 22, thereby providing a hook and loop type of attachment or coupling between the two.

With the toe in a dorsiflexed position, the patient moves the hallux 302 to apply force against the resistance of the third strap or elastic band member 108 to move the hallux 302 from a dorsiflexed position toward a plane generally parallel to a plantar plane of the foot 300 for actively exercising the intrinsic muscles under the foot 300 or connected to the hallux 300, i.e., the hallux longus (calf muscle) and the hallux brevis. These are muscles that are essential to proper push (toe) off in a normal gait pattern. In one embodiment, this exercise modality typically begins at day two after the surgery, but this is determined by the surgeon. As noted above, this configuration is for exercise only, and once the exercise is completed, hallux control strap 52 is put in a hallux valgus control or varus configuration 210, as delineated above, or in hallux plantar plane splinting position 230, as delineated below.

In one embodiment, various strapping configurations allow for a range of digital flexion motions and angles. As a non-limiting example, hallux control strap 52 can thus be used, e.g., to provide up to about a −30 degree plantar flexion angle to about a +60 degree dorsiflexion angle, both while stabilizing the hallux 302 in an optimal zero degree valgus angle Plantar Plane Splinting Configurations Referring to FIG. 16, and also back to FIGS. 5 through 8B, in several other further configurations, hallux control strap system 20 provides hallux plantar plane splinting configuration 230. In this configuration (and other similar configurations), calibrated mid-foot compression strap 22 of hallux control strap system 20 is applied to the foot 300 of the patient as delineated above. Next, hallux control strap 52 is operatively applied to the foot 300 of a patient by placing concave inner surface 100 of hallux pocket or concave portion 98 on or against the front and top or dorsum side of the hallux 302 before or after first elongated strap member 54 is threaded or passed through slit 77 of second elongated strap member 74 (or, e.g., first elongated strap member 54 is passed over or under second elongated strap member 74) for forming cruciate strap configuration 94, and placing the intersection of the crossing of first and second elongated strap members 54 and 74 along the bottom or plantar side of the foot 300. First elongated strap member 54 is extended from hallux pocket or concave portion 98 along the medial side of the hallux 302 and then to the intersection under the plantar side of foot 300 and second elongated strap member 74 is extended from hallux pocket or concave portion 98 along the lateral side of the hallux 302 and then to the intersection of cruciate strap configuration 94 located under the plantar side of the foot 300. First and second elongated strap members 54 and 74 are divergently extended from the intersection in a V-shaped pattern and then terminate to first and second free end portions 70 and 90 utilized by the user to tension the respective first and second elongated strap members 54 and 74 of cruciate strap configuration 94 and to secure respective first and second elongated strap members 54 and 74 to calibrated mid-foot compression strap 22. This is done by coupling or attaching respective under surface hook portions 72 and 92 of first and second elongated strap members 54 and 74 to outer loop surface 28 of elongated elasticized body 24 of calibrated mid-foot compression strap 22. In one embodiment, first and second free end portions 70 and 90 are generally attached or coupled to plantar outer surface 48 (FIG. 2) of calibrated mid-foot compression strap 22. With this coupling or attachment, component forces of first and second elongated strap members 54 and 74 sum together and generally extend down the plantar side of the foot 300 with component forces in the valgus and varus direction generally canceling one another. Next, the third strap or elastic band member 108 is tensioned and positioned over the bottom or plantar side of the hallux 302 and over crossing 96 of cruciate strap configuration 94 and then attached plantarly to calibrated mid-foot compression strap 22, to apply an additional force or pressure to the hallux 302 which places the hallux 302 in a plantarflexed position. This attachment or coupling is provided by under surface hook portion 118 of third free end portion 116 of the third strap or elastic band member 108 dorsally attaching or coupling to outer loop surface 28 of elongated elasticized body 24 of calibrated mid-foot compression strap 22, thereby providing a hook and loop type of attachment or coupling between the two.

Hallux plantar plane splinting configuration 230 of hallux control strap system 20 increases the range of motion of the hallux 302 in the plantar plane, which allows for the creation of the strength for push off in gait. Any joint has strength only in its range of motion but not at the end of the range of motion. Proper push off of the hallux 302 reduces the incidence of other complications such as metatarsalgia in the second toe 304 and plantar plate disruption of the second toe 304, both of which occur due to too much force being placed on the second toe 304 because the hallux 302 has a diminished weight and force bearing roll due to lack of strength or range of motion. Accordingly, hallux plantar plane splinting configuration 230 is important for normal gait.

In one embodiment, splinting and exercising of the hallux 302 is needed for 6-8 weeks following bunionectomy surgery. This is a time frame the body needs for proper healing. Without proper soft tissue care by correctly aligning the hallux 302 and exercising the supporting musculature, the surgical repair has a higher complication rate and a higher potential for additional surgical intervention or eventual pain and malalignment of the hallux 302.

Osteotomy Strap Systems

Figure 3:
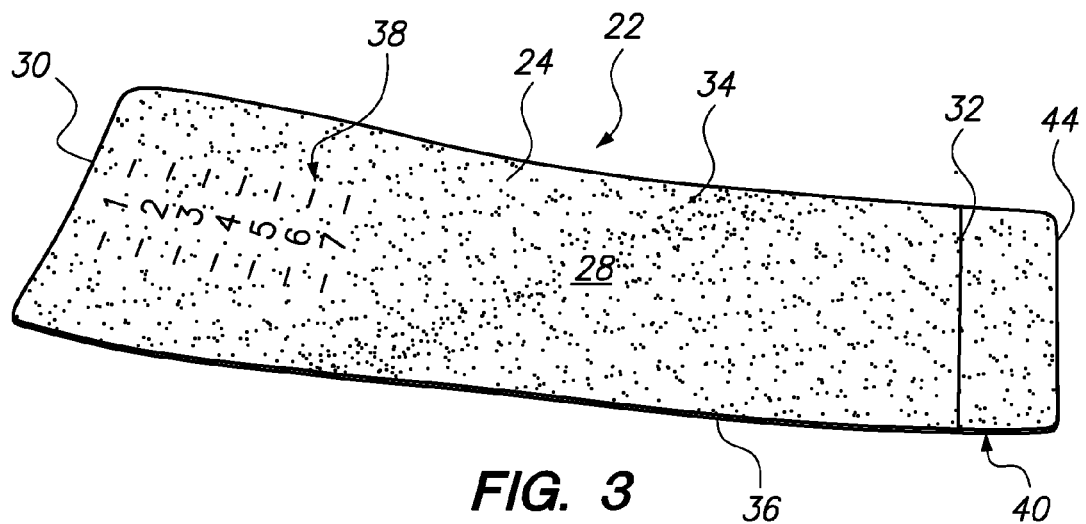
FIG. 3 is a top perspective view of an embodiment of an unwrapped calibrated mid-foot compression strap, of the hallux control strap system illustrated in FIG. 1.

Referring now to FIGS. 17 through 20 and back to FIGS. 3 and 4, and in one embodiment, a digital or toe strapping system is comprised of osteotomy strap system 120. Osteotomy strap system 120 is comprised of calibrated mid-foot compression strap 22 (and/or e.g., a circumscribing member, sleeve and/or sock) and T-shaped osteotomy strap 122. T-shaped osteotomy strap 122 is comprised of an upper or toe strap member 124 that wraps circumferentially around one or more toes and, in one embodiment, around the body of the second toe 304 and/or third toe 306 of the foot 300 and an elongated lower or base strap member 144, which is preferably integrally formed with upper or toe strap member 124 and which attaches to calibrated mid-foot compression strap 22 in a osteotomy plantar plane splinting configuration 240 for placing a second toe 304 and/or a third toe 306 of the foot 300 in a plantar flexed position.

Upper or toe strap member 124 wraps completely and snugly around the entire circumference of the second toe 304 and/or the third toe 306, making sure that lower longitudinal edge 138 of upper or toe strap member 124 is seated at the base of the toe space so the application of force is on the metatarsophalangeal (solely or primarily), or all toe joints, or along nearly the entire length of the second toe 304 and/or the third toe 306 (or in an alternate embodiment at least along ⅓ or ½ its length), which splints the second toe 304 and/or the third toe 306 straight. Unlike a basic elastic loop, it first allows splinting by keeping the joints of the toe from flexing. It second affords such splinting and movement of the entire toe all together and in a particular direction, which is in accordance with the angle of attachment of elongated lower or base strap member 144 to a particular position of the foot 300 (e.g., on outer loop surface 28), as indicated by any combination of movements along transverse lateral-medial bi-directional arrows Y and posterior-anterior bi-directional arrows Z. This angle of attachment is such that the tensioning of upper or toe strap member 124 pulls the second toe 304 and/or the third toe 306 into about a −5 degree angle in the plantar direction with respect to a line coaxial with a normal, healthy, straight position of the toe. However, at least one embodiment allows movement between a 0-20° angle with respect to the plantar plane (by stretching along direction arrows Z), and between 0-80° (or about 0-20°, or 0-50°) with respect to the toe's metatarsal axes (by rotating along direction arrows Y). As such, upper or toe strap member 124 wraps around each lesser toe (or digit) substantially or nearly perpendicular, or perpendicular, to the plane defined by elongated lower or base strap member 144. Also assisting in this function is that upper or toe strap member 124 and elongated lower or base strap member 144 are coplanar and made from a single piece of material, though this is not required in each embodiment.

Figure 17:
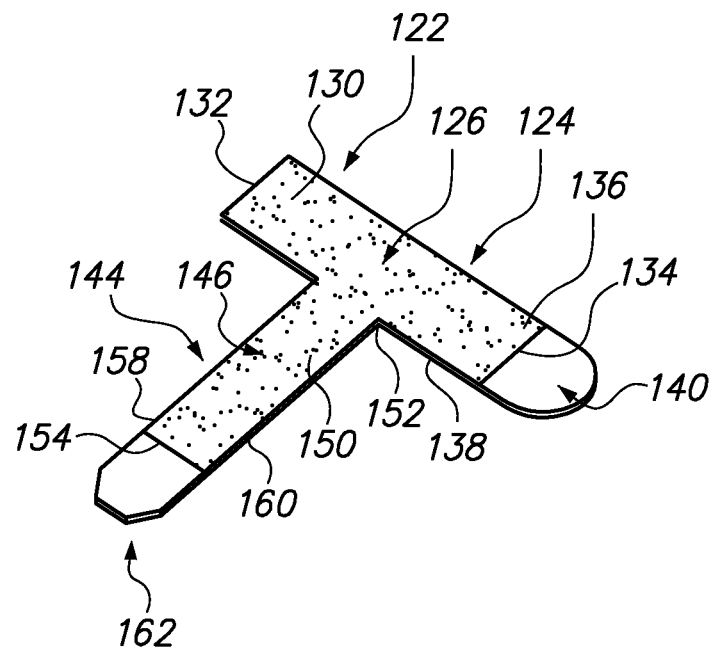
FIG. 17 is an anterior perspective view of an embodiment of a T-shaped osteotomy splinting strap of an osteotomy strap system.
Figure 18:
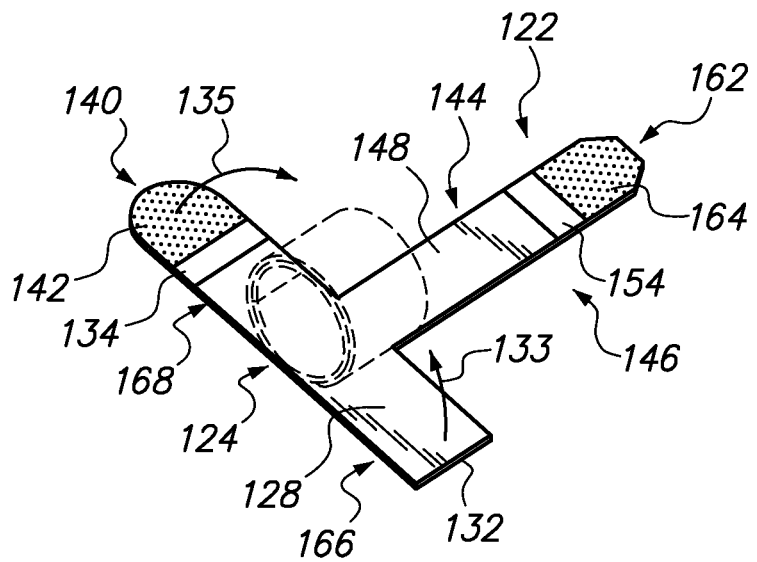
FIG. 18 is a posterior perspective view of the T-shaped osteotomy splinting strap of FIG. 17 of an osteotomy strap system wherein phantom lines indicate one embodiment of a toe-attachment configuration.
Figure 19:
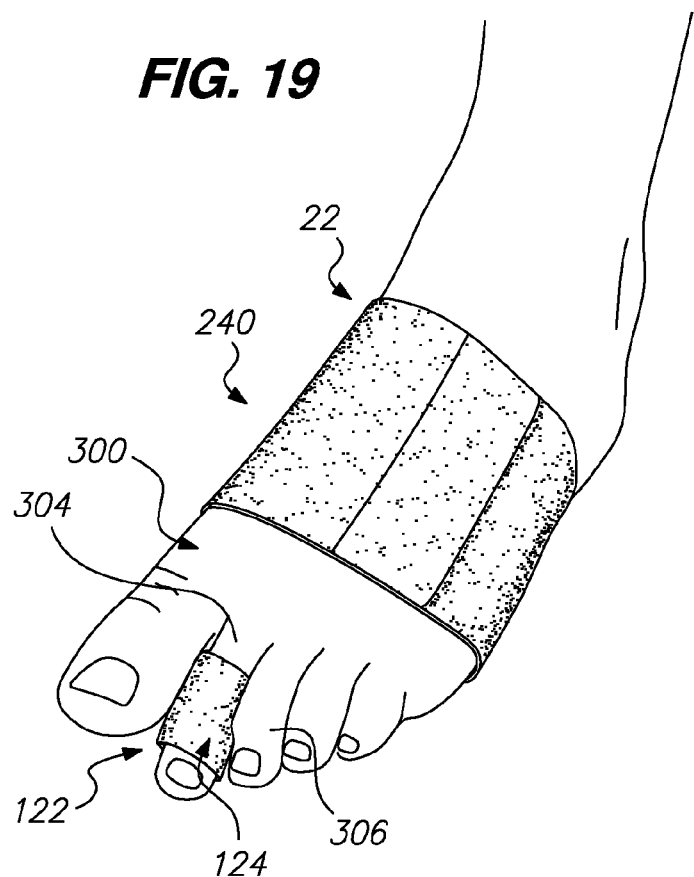
FIG. 19 is a top perspective view of an embodiment of an osteotomy strap system comprising the calibrated mid-foot compression strap of FIG. 5 without calibration indicia, and the T-shaped osteotomy splinting strap of FIG. 18 applied to the foot of the patient in one embodiment of an osteotomy plantar plane splinting configuration.

More specifically, and referring to FIGS. 17 and 18, the upper or toe strap member 124 is comprised of an elongated elasticized body 126 having an inner surface 128, an outer loop surface 130, opposing first and second ends 132 and 134, and opposing upper and lower longitudinal edges 136 and 138. In this embodiment, osteotomy strap system 120 is not merely a single unit that positions one or more of the lesser toes (or digits) in a plantar flexed position. Oseotomy strap system 120 has the added capability to apply a splinting force on the toe(s) in a specific direction. This is important for several reasons. Particularly with the second toe 304 (or digit or ray), when the hallux 302 is in a valgus position a force that merely positions the lesser toes (or digits) (e.g., the second toe 304) in a plantar flexed position also puts the second toe 304 into a valgus position. If the proximal end(s) of the toe (or toes) are pulled in a downward and rearward motion the metatarsal angle has been compromised into a higher valgus angle and any rearward tensioning on the second toe 304 will actually exacerbate the toe angle and create more valgus on the second toe 304, which is exactly opposite from what should occur when applying an appropriate splinting force, which is to reduce the metatarsal angle between the toes to have a straighter alignment. Thus, the particular structure of this embodiment provides a splinting force that does not create lesser digit valgus.

Inner surface 128 is formed from, but not limited to, a soft hypoallergenic non-slip material that provides a soft but tactile (high coefficient of friction) interface with the skin for minimizing migration of T-shaped osteotomy strap 122. Additionally, outer loop surface 130 is entirely comprised of a loop type of material defining outer loop surface 130. One type of material that provides the soft hypoallergenic non-slip inner surface 128 and outer loop surface 130 of elongated elasticized body 126 is, but not limited to, a material referenced as KT-PS-01 Knew-Tek™ Pigskin Black and sold by HTI Global, Inc., 15 West Finch Street, Broadalbin, N.Y. 12025.

Upper or toe strap member 124 is further comprised of end portion 140 attached by, but not limited to, machine or hand stitching to second end 134 of elongated elasticized body 126 of upper or toe strap member 124. End portion 140 comprises under surface hook portion 142 compatible with outer loop surface 130 of elongated elasticized body 126 of upper or toe strap member 124 for forming a hook and loop type of coupling or attachment with outer loop surface 130 when upper or toe strap member 124 wraps circumferentially around one or more toes via paths 133 and 135 illustrated in FIG. 18, and specifically, around the body of the second toe 304 and/or the third toe 306 of the foot 300.

Elongated lower or base strap member 144 is comprised of an elongated elasticized body 146 having an inner surface 148, an outer loop surface 150, opposing first and second ends 152 and 154, and opposing inner and outer longitudinal edges 158 and 160.

Inner surface 148 is preferably formed from, but not limited to, a soft hypoallergenic non-slip material that provides a soft but tactile (high coefficient of friction) interface with the skin for minimizing migration of T-shaped osteotomy strap 122 and outer loop surface 150 is entirely comprised of a loop type of material defining outer loop surface 150. One type of material that provides soft hypoallergenic non-slip inner surface 148 and outer loop surface 150 of elongated elasticized body 146 of elongated lower or base strap member 144 is, but not limited to, a material referenced as KT-PS-01 Knew-Tek™ Pigskin Black and sold by HTI Global, Inc., 15 West Finch Street, Broadalbin, N.Y. 12025.

Additionally, first end 152 of elongated elasticized body 146 of elongated lower or base strap member 144 is integrally formed with a medial portion of lower longitudinal edge 138 of upper or toe strap member 124 such that in an on-rolled configuration upper or toe strap member 124 is divided into first and second sections 166 and 168 such that first section 166 extends in one direction substantially at right angles to elongated lower or base strap member 144 and such that second section 168 extends in a direction opposite said one direction and at substantially right angles to elongated lower or base strap member 144.

Furthermore, elongated lower or base strap member 144 is further comprised of end portion 162 attached by, but not limited to, machine or hand stitching to second end 154 of elongated elasticized body 146 of elongated lower or base strap member 144. End portion 162 has an under surface hook portion 164 compatible with outer loop surface 28 of elongated elasticized body 24 of calibrated mid-foot compression strap 22 for forming a hook and loop type of removable coupling or attachment between the two.

In use and operation, and referring to FIGS. 17 through 20, in one embodiment osteotomy strap system 120 is applied in an osteotomy plantar plane splinting configuration 240 by steps including applying calibrated mid-foot compression strap 22 to the mid-foot of the patient as delineated above; locating upper or toe strap member 124 of T-shaped osteotomy strap 122 under the body of the second toe 304 and/or the third toe 306 of the foot 300 such that the soft but tactile inner surface 128 faces the skin of the second toe 304 and/or the third toe 306 and elongated lower or base strap member 144 posteriorly extends toward the heel of the foot 300. First section 166 of upper or toe strap member 124 is wrapped around the lateral side of the second toe 304 and/or third toe 306, and second section 168 is wrapped around the medial side of the second toe 304 and/or the third toe 306. Under surface hook portion 142 of end portion 140 is attached to outer loop surface 130 of elongated elasticized body 126 of upper or toe strap member 124 for encircling the second toe 304 and/or the third toe 306 of the foot 300 with upper or toe strap member 124. It further includes tensioning elongated lower or base strap member 144 to place the second toe 304 and/or the third toe 306 of the foot 300 into a plantarflexed position, and attaching under surface hook portion 164 of elongated lower or base strap member 144 to outer loop surface 28 of elongated elasticized body 24 of calibrated mid-foot compression strap 22 at a location that splints the second toe 304 and/or the third toe 306 of the foot 300 in a plantarflexed position.

In this osteotomy plantar plane splinting configuration 240, osteotomy strap system 120 holds the surgical toe in a plantarflexed position so that the scarring that takes place does so in a manner that precludes dorsal drift and a condition known as floating toe, which is a condition where the surgical toe raises up superior to the other toes, thereby creating a problem for the foot 300 to fit into footwear. Additionally, osteotomy strap system 120 can easily be worn in a walking boot, post-op shoe, or normal footwear and may also be used non-operatively to treat metatarsalgia.

In one embodiment, osteotomy strap system 120 is worn for the first 6-8 weeks following surgery until the soft tissue is healed. Osteotomy strap system 120 is worn at least throughout the night and also, preferably, during the day. Soft but tactile inner surfaces 128 and 148 of the T-shaped osteotomy strap 122 provide a soft yet strong resilient material to hold the surgical toe in a neutral position or a plantar flexed position for extended periods of time without causing skin abrasion or skin breakdown that result in unsuccessful rehabilitation of the post-surgical toe. The adjustable upper or toe strap member 124 allows effective capturing and securing of the post-surgical toe.

Referring now to FIGS. 21 through 24 and back to FIGS. 3 and 4, and in one embodiment, osteotomy strap system 120 is further comprised of an osteotomy exercise strap system 170. Osteotomy exercise strap system 170 is comprised of calibrated mid-foot compression strap 22 (and/or other foot securing feature, such as shown above and below) and a T-shaped osteotomy exercise strap 172. T-shaped osteotomy exercise strap 172 is comprised of an upper or toe strap member 174 that wraps circumferentially around one or more toes via paths 183 and 185 illustrated in FIG. 22 and, specifically, around the body or proximal shaft of the second toe 304 and/or the third toe 306. T-shaped osteotomy exercise strap 172 is further comprised of a lower strap or elastic band member 198, which is attached to upper or toe strap member 174 and which is removably coupled to calibrated mid-foot compression strap 22 in an osteotomy exercise configuration 250 for placing the second toe 304 and/or the third toe 306 of the foot 300 in a dorsiflexed position and providing resistance, against which the second toe 304 and/or the third toe 306 can apply a force to move from the dorsiflexed position toward a plantar plane of the foot 300 for actively exercising at least the surgical toe for increasing the strength in the surgical toe thereby improving function therein.

More specifically, upper or toe strap member 174 is comprised of an elongated elasticized body 176 having an inner surface 178, an outer loop surface 180, opposing first and second ends 182 and 184, and opposing upper and lower longitudinal edges 186 and 188.

Inner surface 178 is formed from, but not limited to, a soft hypoallergenic non-slip material that provides a soft but tactile (high coefficient of friction) interface with the skin for minimizing migration of T-shaped osteotomy exercise strap 172. Additionally, outer loop surface 180 is entirely comprised of a loop type of material for defining outer loop surface 180. One type of material that provides the soft hypoallergenic non-slip inner surface 178 and outer loop surface 180 of elongated elasticized body 176 is, but not limited to, a material referenced as KT-PS-01 Knew-Tek™ Pigskin Black and sold by HTI Global, Inc., 15 West Finch Street, Broadalbin, N.Y. 12025.

Upper or toe strap member 174 is further comprised of an end portion 190 attached by, but not limited to, machine or hand stitching to second end 184 of elongated elasticized body 176 of upper or toe strap member 174. End portion 190 comprises an under surface hook portion 192 compatible with outer loop surface 180 of elongated elasticized body 176 of upper or toe strap member 174 for forming a hook and loop type of coupling or attachment with outer loop surface 180 when upper or toe strap member 174 wraps circumferentially around one or more toes via paths 183 and 185 illustrated in FIG. 22 and, specifically, around the body or proximal shaft of the second toe 304 and/or the third toe 306 of the foot 300.

Figure 25:
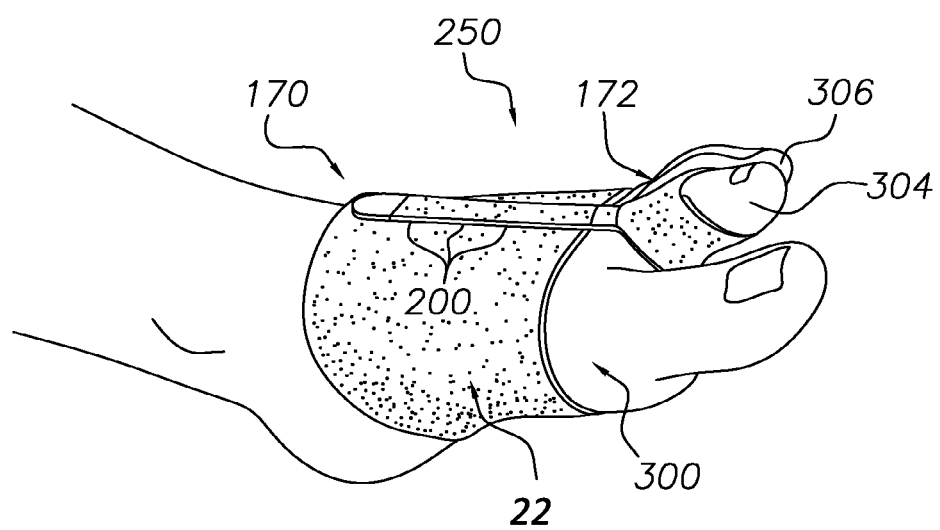
FIG. 25 is a top and side perspective view of an embodiment of an osteotomy strap system comprised of an osteotomy exercise strap having a plurality of elastic exercise bodies.

In one embodiment, each lower strap or elastic band member 198 is comprised of at least one elasticized body 200 extending between a first end 202 and a second end 204. In one embodiment, each elasticized body 200 is formed from, but not limited to, a blend of nylon and an elastomer such as that sold under the LYCRA® trademark. FIG. 25 illustrates an embodiment of lower strap or elastic band member 198 comprised of a plurality of elasticized bodies 200 for providing a higher level of resistance.

Additionally, first end 202 of each elasticized body 200 is attached by, but not limited to, machine or hand stitching to a medial portion of lower longitudinal edge 188 of elongated elasticized body 176 of upper or toe strap member 174 such that in an on-rolled configuration, upper or toe strap member 174 is divided into first section 194 and second section 196 such that first section 194 extends in one direction and second section 196 extends in a direction opposite said one direction.

Furthermore, an end portion 206 is attached by, but not limited to, machine or hand stitching to each second end 204 of each elongated elastic body 200 of each lower strap or elastic band member 198. End portion 206 comprises under surface hook portion 208 compatible with the loop type of material of outer loop surface 28 of elongated elasticized body 24 of calibrated mid-foot compression strap 22 for forming a hook and loop type of removable coupling or attachment between the two.

In use and operation, and referring to FIGS. 21 through 25, in one embodiment osteotomy exercise strap system 170 is applied in osteotomy exercise configuration 250 by the steps including, applying calibrated mid-foot compression strap 22 to the mid-foot of the patient as delineated above; locating upper or toe strap member 174 over the body of the second toe 304 and/or the third toe 306 of the foot 300 such that soft but tactile inner surface 178 faces the skin of the toe or toes (or digit or digits) and the lower strap or elastic band member 198 extends posteriorly along the dorsal side of the foot 300; wrapping first section 194 of upper or toe strap member 174 around the second toe 304 and/or the third toe 306 of the foot 300, starting along the lateral side of the second toe 304 or the third toe 306; wrapping second section 196 around the second toe 304 and/or the third toe 306, starting along the medial side of the second toe 304 or the third toe 306; attaching under surface hook portion 192 of end portion 190 to outer loop surface 180 of elongated elasticized body 176 of upper or toe strap member 174 for encircling the second toe 304 and/or the third toe 306 of the foot 300 with upper or toe strap member 174; tensioning at least one lower strap or elastic band member 198 to pull the second toe 304 and/or the third toe 306 of the foot 300 into a dorsiflexed position; and attaching under surface hook portion 208 of at least one lower strap or elastic band member 198 under tension to outer loop surface 28 of elongated elasticized body 24 of calibrated mid-foot compression strap 22 at a location that tensions the second toe 304 and/or the third toe 306 of the foot 300 in the dorsiflexed position.

In the process of rehabilitation, osteotomy exercise strap system 170 can employ lower strap or elastic band member 198 having one or more elasticized bodies 200 for varying resistance for use in a strengthening program that starts out with a low resistance level using a single elasticized body 200 and with low repetitions and works up either through more repetitions and/or more resistance via a plurality of elasticized bodies 200. Typically the surgical toe is the second toe 304, but sometimes the osteotomy is done on both the second toe 304 and the third toe 306. If the second toe 304 is the surgical toe, T-shaped osteotomy exercise strap 172 can be applied to the second toe 304 as described above or, if the second toe 304 does not have enough initial strength, T-shaped osteotomy exercise strap 172 can be applied to the second toe 304 and to the third toe 306 to put them together during exercise.

With at least the surgical toe in the dorsiflexed position, the patient moves at least the surgical toe to apply force against the resistance of one or more elasticized bodies 200 to plantar flex at least the surgical toe for actively exercising the tendons and ligaments associated with at least the surgical toe. An exercise program may include exercising one or more times a day by utilizing a T-shaped osteotomy exercise strap 172 comprising a single elasticized body 200 or a plurality of elasticized bodies 200. For example, the exercise program may initially utilize a T-shaped osteotomy exercise strap 172 comprising a single elasticized body 200 for performing three sets of 10 plantar flexes twice a day and then three sets of 10 plantar flexes three times a day then three sets of 15 plantar flexes three times a day and then utilize T-shaped osteotomy exercise strap 172 comprising a plurality (e.g., three) of elasticized bodies 200 (FIG. 25) for providing multiple (e.g., three) times the resistance for use in the above protocol of sets and repetitions, thereby providing a postoperative rehabilitation program for the foot 300 so the patient can go back into a normal walking position.

In one embodiment, any or all of the above and below-described hallux and/or osteotomy embodiments alternately include less than entire surface coverage of calibrated mid-foot compression strap 22 by hook and/or loop fabric, but nevertheless afford attachment of straps or bands along nearly their full, or their full, longitudinal and/or latitudinal surfaces. For example, intermittently spaced patches, circles, stripes, or panels of attachment surface are also suitable.

Figure 26:
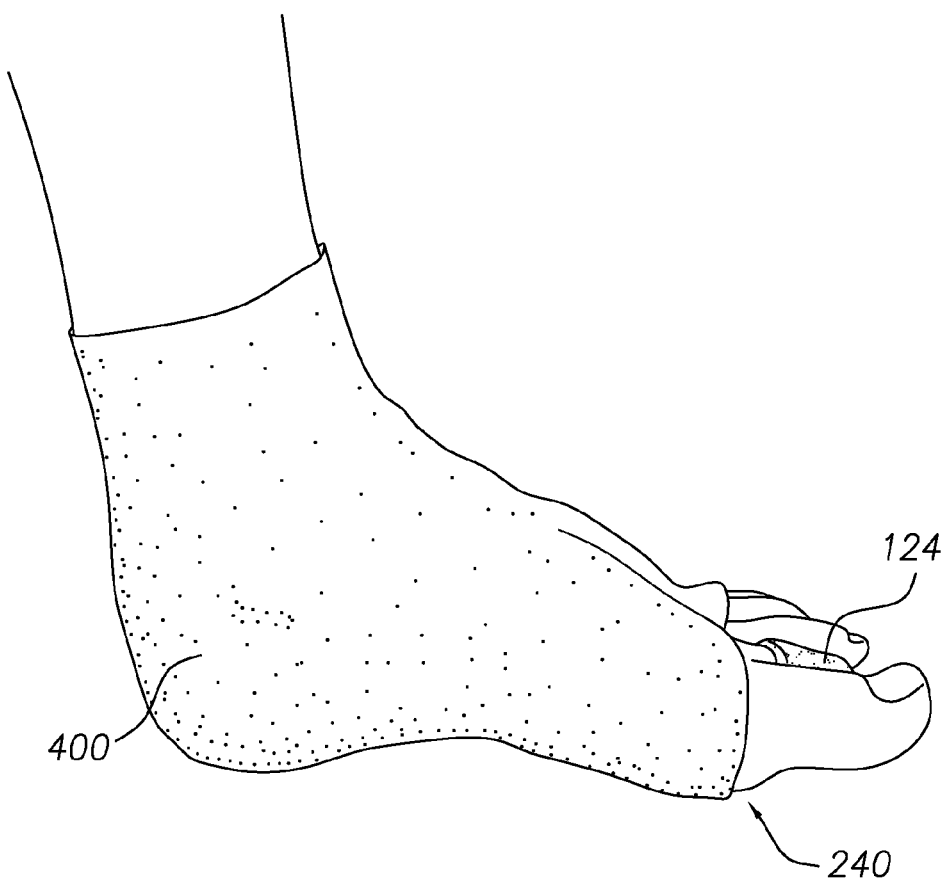
FIG. 26 is a medial side perspective view of an embodiment of an osteotomy strap system comprising one embodiment of a compression sock and the T-shaped osteotomy splinting strap of FIG. 17 applied to a foot of a patient in one embodiment of an osteotomy plantar plane splinting configuration.
Figure 27:
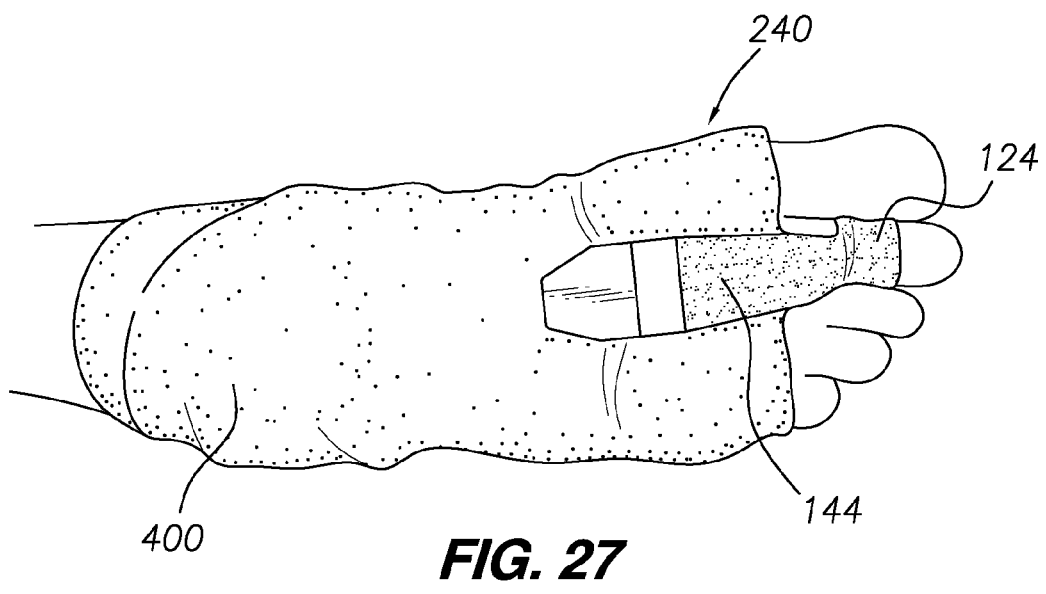
FIG. 27 is a bottom view of the osteotomy strap system of FIG. 26.

Referring to FIGS. 26 and 27, in one embodiment elongated lower or base strap member 144 attaches to a compression sleeve 400 to provide an osteotomy plantar plane splinting configuration 240 by splinting and redirecting a toe with upper or toe strap member 124.

Figure 28A:
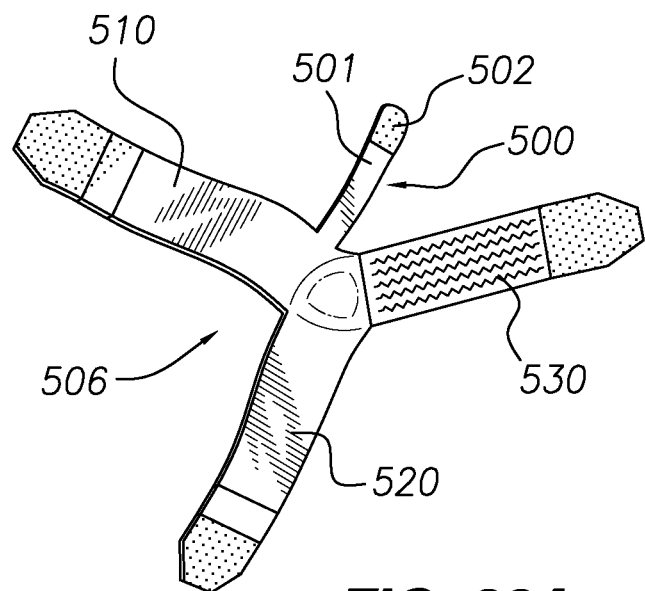
FIG. 28A is a posterior perspective view of an embodiment of a hallux control strap of a hallux control strap system.
Figure 28B:
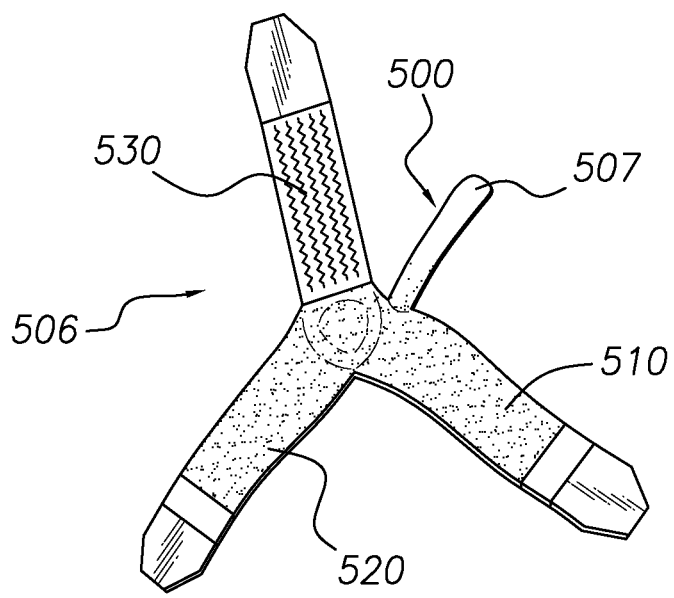
FIG. 28B is an anterior perspective view of the hallux control strap of FIG. 28A of a hallux control strap system.

Referring to FIGS. 28A and 28B, in one embodiment, hallux control strap 506 has a toe connection strap 500, including a longitudinal wrapping member 501, an inner side end attachment portion 502, and an outer side strap receiving portion 507. Otherwise, hallux control strap 506 is, but need not be, substantially the same as hallux control strap 52. In this configuration, a hallux pocket portion is generally centrally located between a first elongated strap member 510, a second elongated strap member 520, and a third strap or elastic band member 530. However, one or more toe connection straps 500 allow added versatility to the number of functionally effective strapping configurations provided by hallux control strap 506 (and alternately to any osteotomy strap). First and second elongated strap members 510 and 520 are attached to and divergently extend away from the hallux pocket portion, thereby forming about a 90 degree angle between first and second elongated strap members 510 and 520, and toe connection strap 500 extends substantially perpendicular from either, or any and all of, first and second elongated strap members 510 and 520. Toe connection strap 500 extends from a location proximal to the attachment position of first elongated strap member 510, but can be positioned anywhere along any of first elongated strap member 510, second elongated strap member 520 and/or third strap or elastic band member 530. Although not absolutely needed, toe connection strap 500 assists in securing first elongated strap member 510, second elongated strap member 520 and/or third strap or elastic band member 530 to a toe, here a hallux, as seen in the FIGS. described below. It nevertheless provides for a more diverse number of hallux pocket placement positions about various portions of a hallux, and similarly provides the same for an osteotomy strap regarding a lesser digit.

Figure 16:
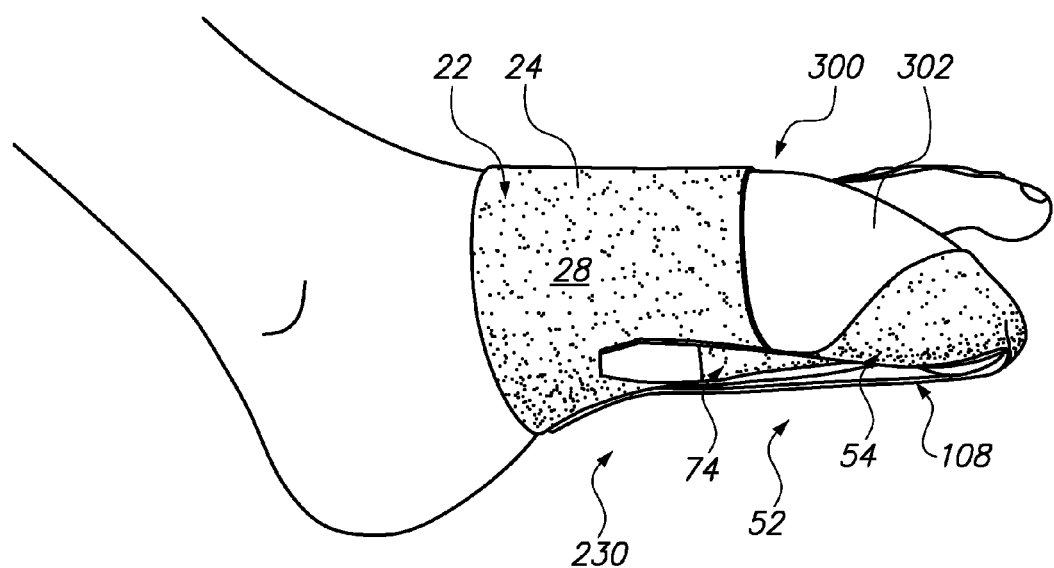
FIG. 16 is a side perspective view of an embodiment of a hallux control strap system applied to a foot of a patient in a hallux plantar plane splinting configuration.
Figure 29:
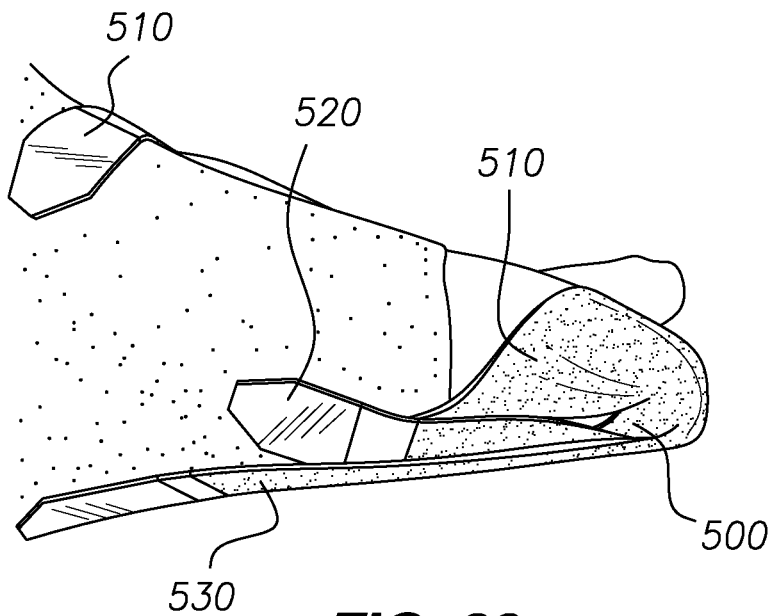
FIG. 29 is a partial medial side view of an embodiment of a hallux control strap system comprising the hallux control strap of FIG. 28A applied to a foot of a patient in another embodiment of a hallux plantar plane splinting configuration.

Referring to FIG. 29, in one embodiment, hallux control strap 506 is attached substantially similar to the attachment described in FIG. 16 except for a few notable exceptions, which are that toe connection strap 500 is wrapped around a hallux and first elongated strap member 510 is stretched tightly and wrapped under the plantar and medial sides, and then over and around an instep.

Figure 30:
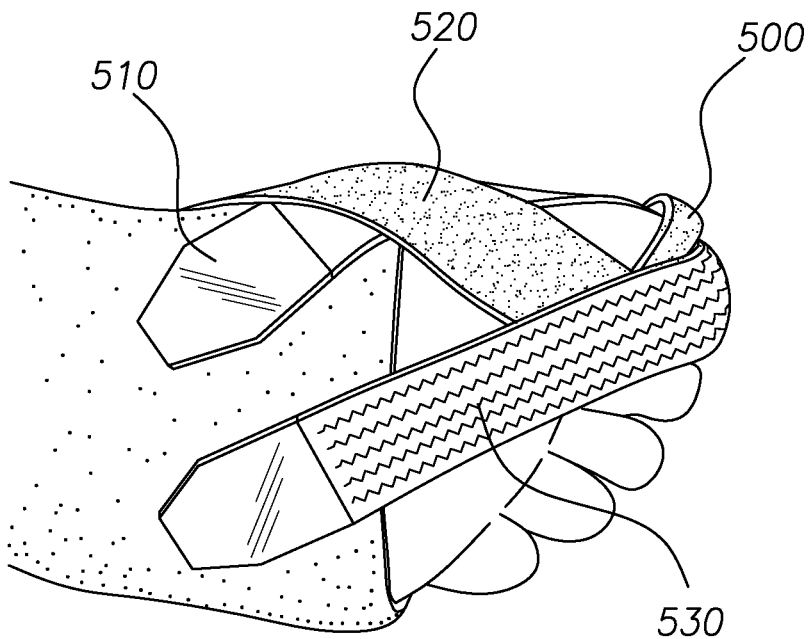
FIG. 30 is partial bottom perspective view of an embodiment of a hallux control strap system comprising the hallux control strap of FIG. 28A applied to a foot of a patient in yet another embodiment of a splinting configuration.

Referring to FIG. 30, in one embodiment first and second elongated strap members 510 and 520, and third strap or elastic band member 530 wrap (i.e., are wrapped) from a hallux pocket portion placed on a hallux toe nail but affixed to the hallux in part by toe connection strap 500. First elongated strap member 510 wraps across a hallux dorsal surface, around a medial side and to a plantar surface of a foot; second elongated strap member 520 wraps between the hallux and lesser digit, under a plantar surface, around a medial side and onto a foot dorsal surface; third strap or elastic band member 530 wraps over the central tip of a hallux, and diagonally across the plantar surface from the medial to the lateral side.

Figure 31:
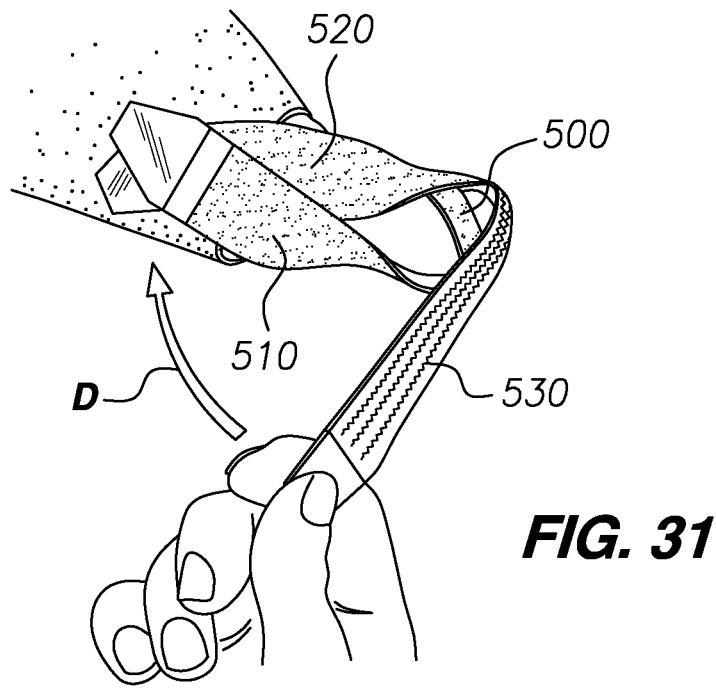
FIG. 31 is a partial medial side view of an embodiment of a hallux control strap system comprising the hallux control strap of FIG. 28A as being applied to a foot of a patient in still another embodiment of a splinting configuration.

Referring to FIG. 31, in one embodiment, first elongated strap member 510 wraps across and around a hallux lateral surface, under the hallux plantar surface and to a medial side of a foot; second elongated strap member 520 wraps between the hallux and a lesser digit, over a dorsal proximal portion of a hallux surface, and around to a medial side of the foot; third strap or elastic band member 530 stretches and wraps per direction arrow D under the central or medial side tip of a hallux (to which outer side strap receiving portion 507 is in part anchored by toe connection strap 500), and pulled to the posterior of the foot for attachment across a central axis of the plantar surface of the foot.

Figure 32:
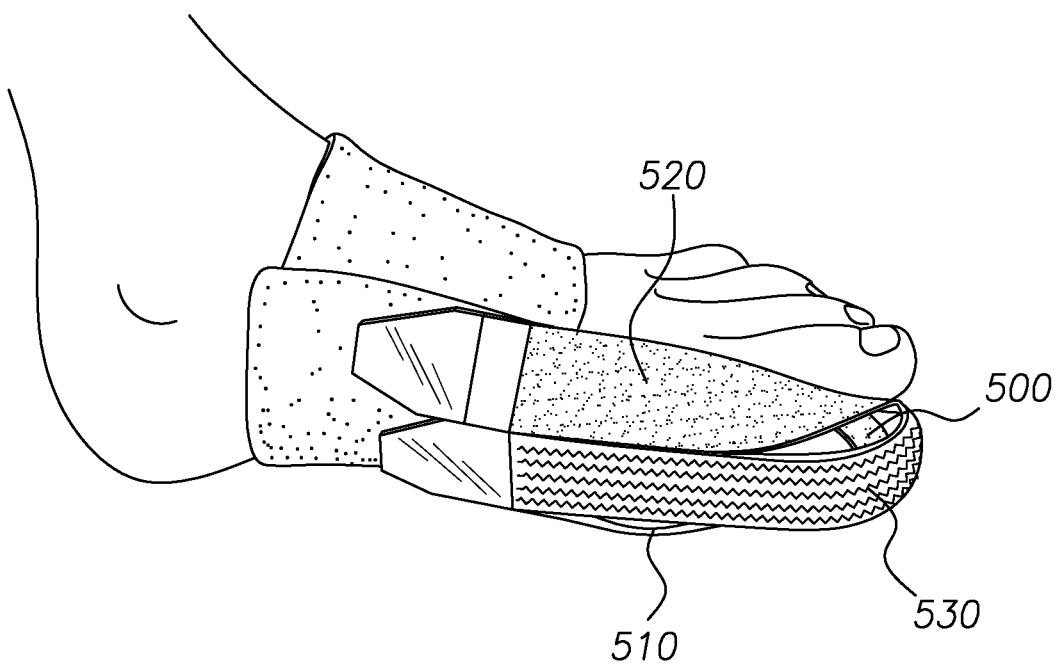
FIG. 32 is a medial side top perspective view of an embodiment of a hallux control strap system comprising the hallux control strap of FIG. 28A applied to a foot of a patient in yet another embodiment of a splinting configuration.

Referring to FIG. 32, in one embodiment, first elongated strap member 510 wraps across and around a hallux lateral surface, under the proximal hallux plantar surface and rearwards to the plantar surface of the foot; second elongated strap member 520 wraps between the hallux and lesser digit, over a dorsal proximal hallux surface, and around a dorsal side of the foot and generally parallel to the foot along a medial side foot surface; third strap or elastic band member 530 stretches and wraps around the lateral, front and medial side tip of a hallux (to which outer side strap receiving portion 507 is in part anchored by toe connection strap 500), and pulled to the posterior of the foot for parallel attachment across a central axis of the medial side surface of the foot. All three of first elongated strap member 510, second elongated strap member 520 and third strap or elastic band member 530 are substantially parallel.

Figure 33A:
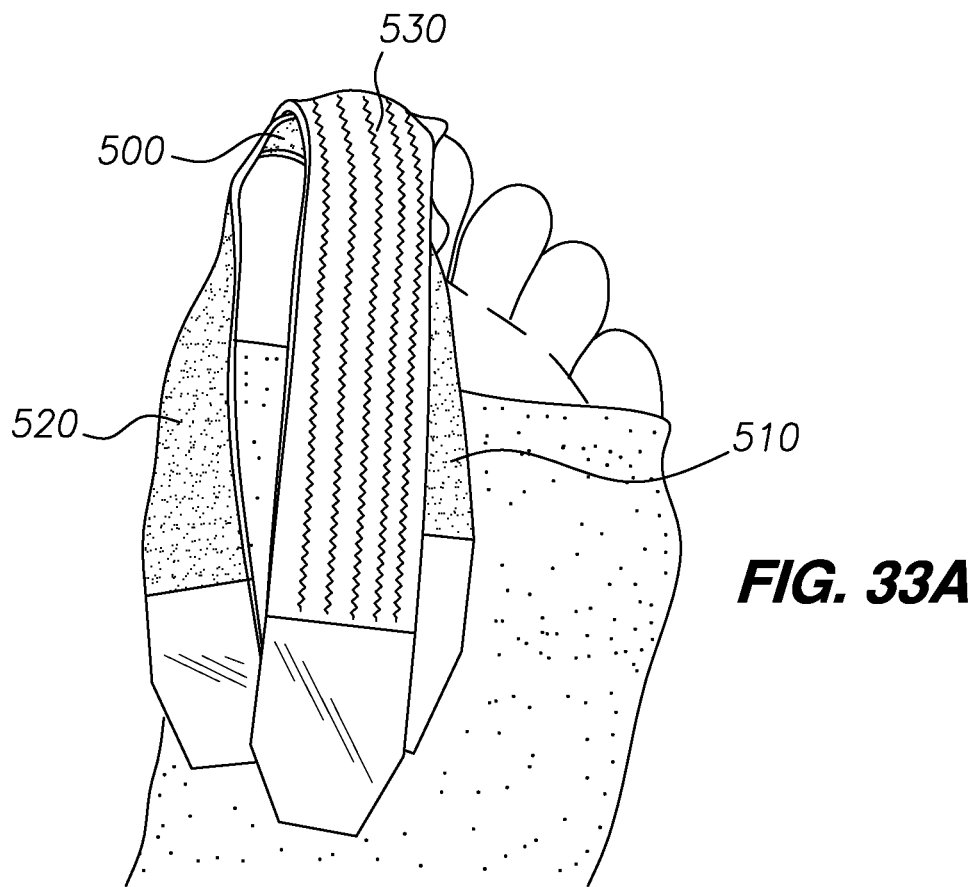
FIG. 33A is a partial bottom perspective view of an embodiment of a hallux control strap system comprising the hallux control strap of FIG. 28A applied to a foot of a patient in still another embodiment of a splinting configuration.
Figure 33B:
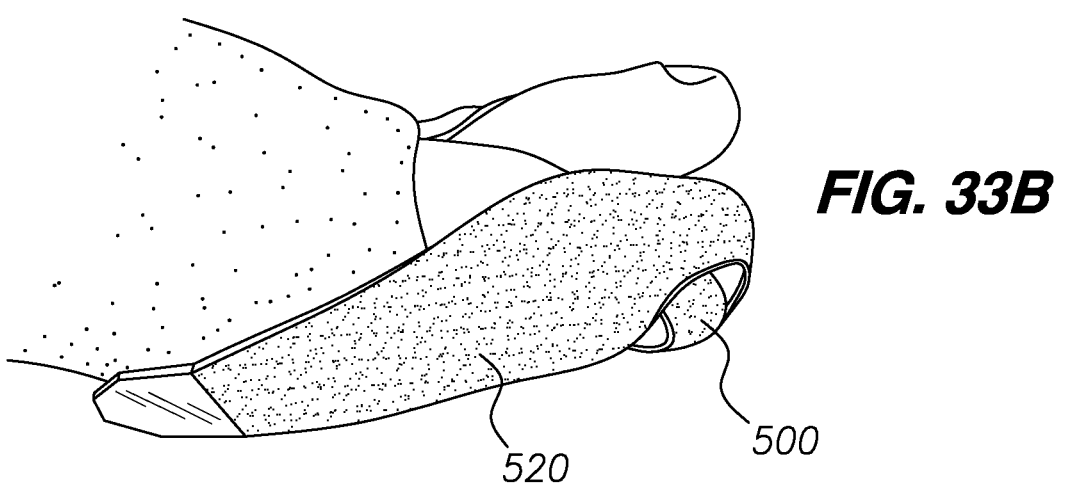
FIG. 33B is a partial side view of the embodiment of the hallux control strap system of FIG. 33A.
Figure 33C:
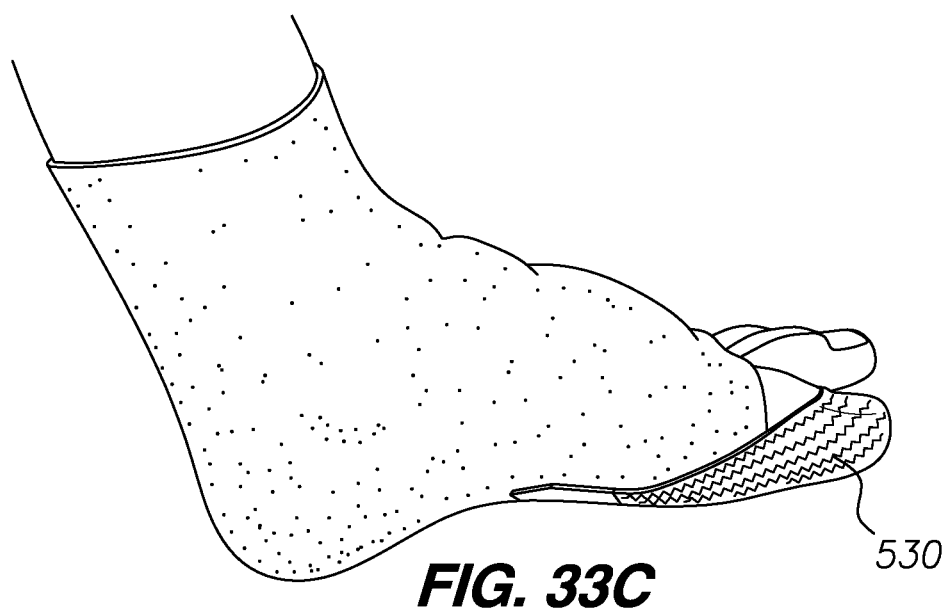
FIG. 33C is a medial side rear perspective view of the embodiment of a hallux control strap system of FIG. 33A.

Referring to FIG. 33A-C, in one embodiment, first elongated strap member 510 wraps along a hallux lateral surface between the hallux and a lesser digit, and rearwardly along a plantar side of a foot; second elongated strap member 520 wraps over the distal front tip and dorsal surface of the hallux, and around a medial side of the foot to a medial-plantar side foot surface; third strap or elastic band member 530 stretches and wraps substantially parallel or parallel under the central plantar surface of the hallux (to which outer side strap receiving portion 507 is in part anchored by toe connection strap 500), and pulled to the posterior of the foot for attachment across a central axis of the plantar surface of the foot. All three of first elongated strap member 510, second elongated strap member 520 and third strap or elastic band member 530 are substantially parallel.

Figure 34A:
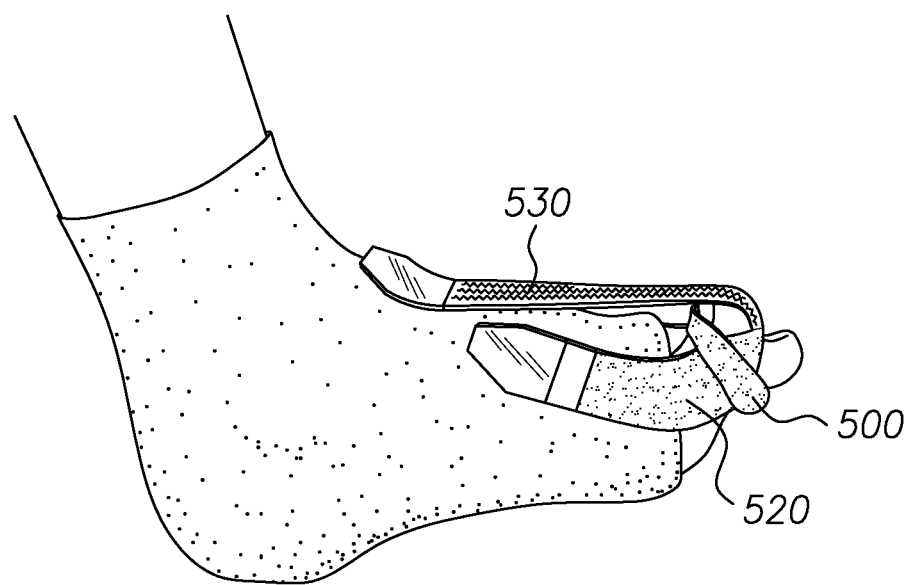
FIG. 34A is a medial side perspective view of an embodiment of a hallux control strap system comprising the hallux control strap of FIG. 28A applied to a foot of a patient in yet another embodiment of a splinting configuration.
Figure 34B:
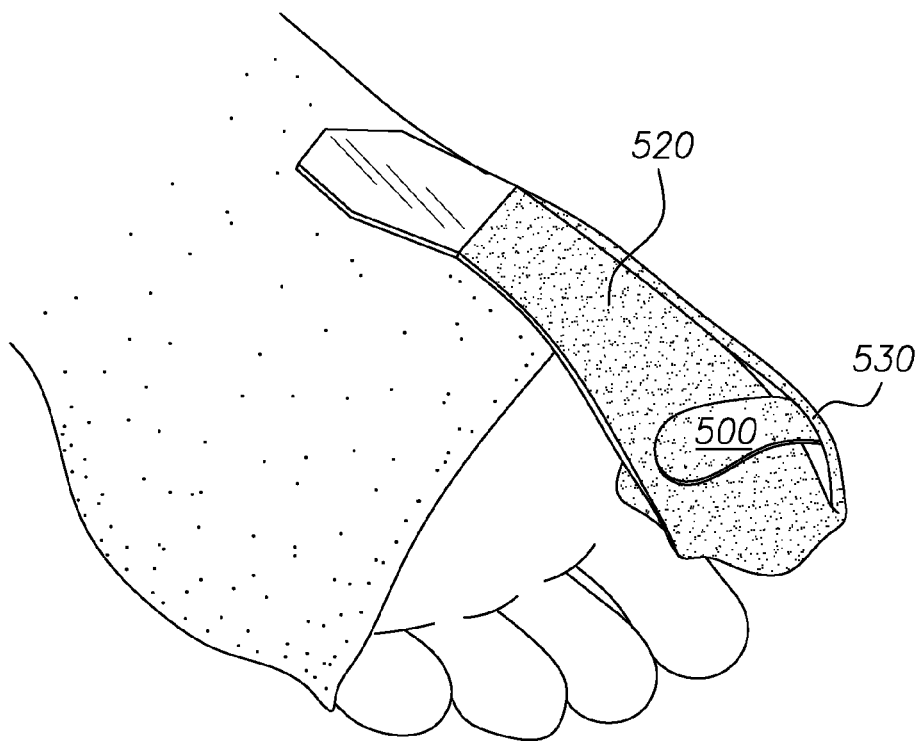
FIG. 34B is a partial bottom view of the embodiment of the hallux control strap system of FIG. 34A.

Referring to FIG. 34A-B, in one embodiment, first elongated strap member 510 wraps across and around a hallux lateral surface, under the proximal hallux plantar surface and to a medial plantar side of a foot; second elongated strap member 520 wraps under the hallux plantar surface, and around a medial side of the foot to a medial-dorsal side foot surface; third strap or elastic band member 530 stretches and wraps directly over the central tip of a hallux (to which outer side strap receiving portion 507 is in part anchored by toe connection strap 500, which overlays second elongated strap member 520 and has mating hook or loop fabric as appropriate to be secured at both its upper and lower surfaces), and pulled to the posterior surface of the foot for attachment across a central axis of the dorsal surface of the foot at the top portion of the instep, wherein the band is tensioned for exercise such that a substantial length of which is not connected to the foot or sleeve. All three of first elongated strap member 510, second elongated strap member 520 and third strap or elastic band member 530 are substantially parallel.

Figure 35:
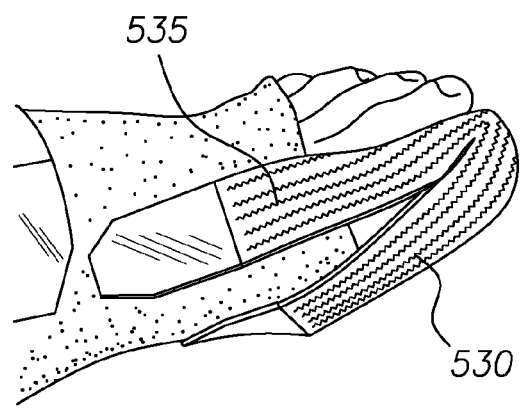
FIG. 35 is a partial medial side perspective view of an embodiment of a hallux control strap system comprising the hallux control strap of FIG. 28A applied to a foot of a patient in still another embodiment of a splinting configuration.

Referring to FIG. 35, in one embodiment, an elastic band 535 replaces second elongated strap member 520. First elongated strap member 510 wraps across and around a hallux lateral surface, under the hallux plantar surface and to a medial side of a foot; elastic band 535 wraps between the hallux and a lesser digit, over a dorsal lower hallux surface, and rearward to the top medial side of the dorsal surface of the instep; third strap or elastic band member 530 stretches and wraps under around the central or medial side tip of a hallux (to which outer side strap receiving portion 507 is in part anchored by toe connection strap 500), and pulled to the posterior of the foot for attachment across the medial side surface of the foot with its end at the plantar medial surface, such that it extends somewhat diagonally downwards. All three of first elongate strap member 510, elastic band 535 (or e.g., second elongated strap member 520 when elastic band 535 is not used) and third strap or elastic band member 530 are substantially parallel.

Thus, as seen in the embodiments of FIGS. 32-35, first and second elongated strap members 510 and 520, and third strap or elastic band member 530 with respect to all of which, or at least with respect to any two of which, form a substantially parallel strap configuration, either on the same medial, dorsal or plantar side of a foot or opposing dorsal and plantar sides of a foot.

In light of the above detailed description, and in one aspect, a digital or toe strapping system is provided that allows a patient or non-patient individual user to stretch and exercise the digits hands free.

In another aspect, an embodiment of the hallux control strap system comprises a calibrated mid-foot compression strap, circumscribing member, sock or sleeve, and a hallux control strap that receives and wraps the hallux in a crisscross strap enclosure and that is dynamically tensioned and coupled medially to the foot via the calibrated mid-foot compression strap, circumscribing member, sock or sleeve for applying additional abduction pressure to the hallux.

In another aspect, an embodiment of the hallux control strap system comprises a hallux control strap that can couple to the foot either plantarly or dorsally via a the calibrated mid-foot compression strap, circumscribing member, sock or sleeve for positioning the hallux plantarly (toward the floor when user is standing), which stretches the hallux extensors or for positioning the hallux dorsally to exercise the plantar flexors of the foot.

In another aspect, an embodiment of the osteotomy strap system comprises a T-shaped osteotomy strap for providing a plantar splinting action and force that originates at the base of the surgical toe so the force is on the metatarsophalangeal joint (MTP).

In another aspect, in an embodiment the osteotomy strap system comprises a T-shaped osteotomy strap for providing, after osteotomy surgery of the second or third digit or toe, proper splinting of the second or third toe in a plantar position required to hold that toe in a healing position so the scarring that takes place does so in a manner that prevents a condition known as floating toe. Floating toe is a condition where the surgical toe raises up superior to the other toes.

In another aspect, the osteotomy strap system comprises a set of osteotomy exercise straps for varying levels of resistances so the patient can progress with increased resistances as the patient progresses for increasing strength in the surgical toe, thereby improving function.

Another aspect of the present invention is directed to a method of hallux control and/or a method of osteotomy therapy that includes any combination of the embodiments, features, components and techniques substantially as described above. Other embodiments, techniques or devices can also or alternately be used in this method aspect, and its various embodiments.

While it is apparent that the illustrative embodiments of the invention disclosed herein fulfill one or more objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

We claim:

1. A digit control strap system, comprising:
   a pocket portion at least a part of which is configured to at least partially receive or abut against a digit of a foot;
   a first strap member extending from the pocket portion and terminating to a first free end;
   a second strap member extending from the pocket portion and terminating to a second free end;
   said first and second strap members configured to cross after extending from the pocket portion and before terminating to the first and second free ends for defining a substantially parallel or cruciate strap configuration extending from the pocket portion and terminating to the first and second free ends, wherein the first and second strap members are alternately configurable to extend at a variety of angles with respect to one another, but are attached to the pocket portion so as to extend at about a 30° angle to about a 180° angle with respect to each other when both are in an unwrapped and unfolded, single coplanar state;
   an elastic band:
      extending from the pocket portion at a location opposing an area of the pocket portion;
      interposed between the first and second strap members; and
      terminating at a third free end; and
   an anchor configured to secure the first and second free ends to a portion of the foot.

2. The digit control strap system of claim 1, wherein the anchor is configured to removably secure the third free end to the foot.

3. The digit control strap system of claim 2, wherein the anchor is configured to be secured to a mid-foot circumscribing member and the anchor includes a first securing portion located on an under surface of the first free end, a second securing portion located on an under surface of the second free end, and a third securing portion located on an under surface of the third free end, the first, second and third securing portions being configured to be removably secured to the mid-foot circumscribing member.

4. The digit control strap system of claim 1, further comprising:
   a toe strap coplanar to the first strap, the second strap, and the elastic band, the toe strap extending transversely from a portion of at least one of the first strap, the second strap, or the elastic band that is proximal to the pocket portion.

5. The digit control strap system of claim 1, wherein the substantially parallel or cruciate strap configuration is cruciate and formed in part by the first strap being configured to stretch tightly and to wrap under the plantar and medial sides of the foot, and then over and around an instep of the foot.

6. The digit control strap system of claim 1, wherein the substantially parallel or cruciate strap configuration is cruciate and formed by the first strap being configured to wrap across a dorsal surface of a digit of the foot, around a medial side of the foot and to a plantar surface of the foot, the second strap being configured to wrap between the digit of the foot and another digit of the foot, under a plantar surface of the foot, around a medial side of the foot and onto the dorsal surface of the foot, an elastic band configured to wrap over a central tip of the digit of the foot, and diagonally across the plantar surface of the foot from the medial side of the foot to the lateral side of the foot.

7. The digit control strap system of claim 1, wherein the substantially parallel or cruciate strap configuration is cruciate and formed by the first strap being configured to wrap across and around a lateral surface of a digit of the foot, under a plantar surface of the digit of the foot and to a medial side of the foot, the second strap being configured to wrap between the digit of the foot and another digit of the foot, over a dorsal proximal portion of a surface of the digit of the foot, and around to a medial side of the foot, an elastic band configured to stretch and to wrap under a central or medial side tip of the digit of the foot and pulled to a posterior of the foot for attachment across a central axis of a plantar surface of the foot.

8. The digit control strap system of claim 1, wherein the substantially parallel or cruciate strap configuration is substantially parallel and formed the first strap being configured to wrap across and around a lateral surface of a digit of the foot, under a proximal plantar surface of the digit of the foot and rearwards to a plantar surface of the foot, the second strap being configured to wrap between the digit of the foot and another digit of the foot, over a dorsal proximal surface of the digit of the foot, and around a dorsal side of the foot and generally parallel to the foot along a medial side surface of the foot, an elastic band configured to wrap around a lateral, front and medial side tip of the digit of the foot, and pulled to a posterior of the foot for parallel attachment across a central axis of a medial side surface of the foot.

9. The digit control strap system of claim 1, wherein the substantially parallel or cruciate strap configuration is substantially parallel and formed by the first strap being configured to wrap along a lateral surface of a digit of the foot between the digit of the foot and another digit of the foot, and rearwardly along a plantar surface of the foot, the second strap being configured to wrap over a distal front tip and dorsal surface of the digit of the foot, and around a medial side of the foot to a medial-plantar side surface of the foot, an elastic band being configured to wrap substantially parallel under a central plantar surface of the digit of the foot, and to extend to a posterior of the foot for attachment across a central axis of the plantar surface of the foot.

10. The digit control strap system of claim 1, wherein the substantially parallel or cruciate strap configuration is substantially parallel and formed by the first strap being configured to wrap along a lateral surface of the digit of the foot between the digit of the foot and another digit of the foot, and rearwardly along a plantar surface of the foot, the second strap being configured to wrap over a distal front tip and dorsal surface of the digit of the foot, and around a medial side of the foot to a medial-plantar side surface of the foot, an elastic band configured to wrap substantially parallel to and under a central plantar surface of the digit of the foot, and to extend to a posterior of the foot for attachment across a central axis of the plantar surface of the foot.

11. The digit control strap system of claim 1, wherein the substantially parallel or cruciate strap configuration is substantially parallel and formed by the first strap being configured to wrap across and around a lateral surface of a digit of the foot, under a plantar surface of the digit of the foot and to a medial side of the foot, a first elastic band configured to wrap between the digit of the foot and another digit of the foot, over a dorsal lower surface of the digit of the foot, and rearward to a top medial side of a dorsal surface of an instep of the foot, a second elastic band configured to wrap under around a central or medial side tip of the digit of the foot, and to extend to a posterior of the foot for attachment across a medial side surface of the foot with an end of the second elastic band configured to be located at medial plantar surface of the foot, such that the end of the second elastic band is configured to extend somewhat diagonally downwards.

12. A digit control strap system, comprising:
   a pocket portion at least a part of which is configured to at least partially receive a digit of a foot;
   a first strap extending from the pocket portion and terminating at a first free end;
   a second strap extending from the pocket portion and terminating at a second free end, the first and second straps being configured to cross after extending from the pocket portion and before terminating at the first and second free ends to define a cruciate strap configuration, the first and second straps being alternately configurable to extend at a variety of angles with respect to one another, and attached to the pocket portion so as to extend at about a 30° angle to about a 180° angle with respect to each other when the first and second straps are in an unwrapped and unfolded, single coplanar state;
   an elastic band extending from the pocket portion and terminating at a third free end; and
   an anchor configured to removably secure the first, second, and third free ends to at least one mid-foot compression strap configured to encircle at least a mid-foot location of a foot.

13. The digit control strap system of claim 12, further comprising:
   a digital strap coplanar to the first strap, the second strap, and the elastic band, the digital strap extending transversely from a portion of at least one of the first strap, the second strap, or the elastic band that is proximal to the pocket portion.

14. The digit control strap system of claim 12, wherein the cruciate strap is configured to selectively overlie a medial side of the foot and the elastic band is configured to overlie a crossing of the cruciate strap to enable adjustable splinting of the digit of the foot in a varus position.

15. The digit control strap system of claim 14, wherein the cruciate strap is configured to selectively overlie a dorsal side of the foot and the elastic band is configured to overlie the crossing of the cruciate strap to enable adjustable positioning of the digit of the foot in a dorsiflexed position, with the elastic band providing resistance against which the digit of the foot is flexed to move from a dorsiflexed position toward a plantar plane of the foot for actively exercising the digit of the foot.

16. The digit control strap system of claim 15, wherein the cruciate strap is configured to overlie a plantar side of the foot and the elastic band is configured to overlie the crossing of the cruciate strap to enable adjustable splinting of the digit of the foot in a plantarflexed position.

17. A digit control strap system, comprising:
a mid-foot circumscribing member configured to encircle at least a mid-foot location of a foot; and
a digital control strap comprising:
a cruciate strap comprising a first strap crossing a second strap, the first and second straps having attached coplanar first ends forming a pocket portion from which the first strap extends in a first direction and terminates at a first free end and from which the second strap extends in a second direction and terminates at a second free end, the first direction being oriented at about a 30° angle to about a 180° angle with respect to the second direction;
an elastic band having a first end attached to the pocket portion and a second free end; and
an anchor configured to secure the second free end of the first strap, the second free end of second strap, and the second free end of the elastic band to the mid-foot circumscribing member.

18. The digit control strap system of claim 17, further comprising:
another digital strap coplanar to the first strap, the second strap, and the elastic band, the another digital strap extending transversely from a portion of at least one of the first strap, the second strap, or the elastic band that is proximal to the pocket portion.

19. The digit control strap system of claim 17, wherein the mid-foot circumscribing member comprises an elongated body with a first end, a second end, an inner surface and an outer surface, the inner surface comprising a non-slip material that provides a soft but tactile interface with skin of the foot to substantially preclude migration of the mid-foot circumscribing member relative to the foot.

20. The digit control strap system of claim 19, wherein the outer surface of the mid-foot circumscribing member comprises calibration indicia correlative to varying levels of compression provided by the mid-foot circumscribing member when circumscribing a foot, the calibration indicia being located proximate to the first end of the mid-foot circumscribing member, the second end of the mid-foot circumscribing member aligning with the calibration indicia at a predetermined level of compression.

21. The digit control strap system of claim 20, wherein the second end of the mid-foot circumscribing member comprises an under surface configured to engage the outer surface of the mid-foot circumscribing member at a location aligning the second end of the mid-foot circumscribing member with the calibration indicia at the predetermined level of compression.

22. The digit control strap system of claim 21, wherein the second free end of the first strap, the second free end of the second strap and the second free end of the elastic band each comprise an under surface configured to reversibly engage an outer surface of the mid-foot circumscribing member.

23. The digit control strap system of claim 22, wherein the first strap comprises an elongated elasticized body having an inner surface comprising a non-slip material that provides a soft but tactile interface with skin of the foot.

24. The digit control strap system of claim 23, wherein the second strap comprises an elongated elasticized body having an inner surface comprising a non-slip material that provides a soft but tactile interface with skin of the foot.

25. The digit control strap system of claim 24, wherein the pocket portion comprises an inner surface comprising a non-slip material that provides a soft but tactile interface with skin of the foot.

26. A digit control strap system, comprising:
a mid-foot circumscribing member configured to encircle at least a mid-foot of a foot of an individual;
a digital strap comprising:
a first element extending in a first direction;
a second element extending in a second direction, away from the first element, the first element and the second element configured to be secured in place over at least one digit of the foot;
a third element extending in a third direction different from the first direction and the second direction, the third element comprising an elastic element attached to and extending from the first element and the second element, the third element having a free end; and
an anchor configured to selectively secure the free end of the third element in place relative to a plantar surface of the mid-foot circumscribing member.

27. The digit control strap system of claim 26, wherein at least one of the first element and the second element comprises an inner surface comprising a non-slip material that provides a soft but tactile interface with skin of the digit.

* * * * *